(12) United States Patent
Bath et al.

(10) Patent No.: US 12,329,906 B2
(45) Date of Patent: *Jun. 17, 2025

(54) SYSTEMS AND METHODS FOR ACTIVE POWER MANAGEMENT IN A MEDICAL DEVICE

(71) Applicant: RESMED PTY LTD, Bella Vista (AU)

(72) Inventors: Andrew Roderick Bath, Sydney (AU); Rudi Voon, Baulkham Hills (AU); David Creusot, Sydney (AU); Dmitri Anatolievich Doudkine, Sydney (AU); Jianhua Zhu, Carlingford (AU); Adam Panarello, Turramurra (AU)

(73) Assignee: ResMed Pty, Ltd., Bella Vista (AU)

( * ) Notice: Subject to any disclaimer, the term of this patent is extended or adjusted under 35 U.S.C. 154(b) by 119 days.

This patent is subject to a terminal disclaimer.

(21) Appl. No.: 17/987,264

(22) Filed: Nov. 15, 2022

(65) Prior Publication Data

US 2023/0080441 A1    Mar. 16, 2023

Related U.S. Application Data

(63) Continuation of application No. 16/600,741, filed on Oct. 14, 2019, now Pat. No. 11,529,481.

(Continued)

(51) Int. Cl.
*A61M 16/00* (2006.01)
*A61M 16/10* (2006.01)
*A61M 16/16* (2006.01)

(52) U.S. Cl.
CPC ...... *A61M 16/0066* (2013.01); *A61M 16/024* (2017.08); *A61M 16/16* (2013.01);
(Continued)

(58) Field of Classification Search
CPC .............. A61M 16/00; A61M 16/0051; A61M 16/0057; A61M 16/0066; A61M 16/0069;
(Continued)

(56) References Cited

U.S. PATENT DOCUMENTS 4,782,832 A    11/1988  Trimble et al.
4,944,310 A    7/1990   Sullivan
(Continued)

FOREIGN PATENT DOCUMENTS

CN    104 815 373 A    8/2015
DE    100 17 193 A1    11/2001
(Continued)

OTHER PUBLICATIONS

"*Respiratory Physiology*", by John B. West, Lippincott Williams & Wilkins, 9th edition published 2012 (8 pages).
(Continued)

*Primary Examiner* — Joseph D. Boecker
(74) *Attorney, Agent, or Firm* — Nixon & Vanderhye, P.C.

(57) ABSTRACT

A respiratory treatment device includes a blower for providing flow of breathable gas to a patient and one or more accessory devices. The respiratory treatment device includes active power management to distribute power from a power source that does not have sufficient power to simultaneously power the blower and the accessory devices. The active power management prioritizes power to the blower and limits, based on current measurements of the blower and the accessory devices, the power supplied to the accessory devices to keep the sum of the power drawn at or below the capacity of the power supply. When additional power is available, due reduced power consumption of the blower, the power to one or more accessory devices is raised beyond a
(Continued)

target in order to compensate for when power was not supplied to the one or more accessory devices.

21 Claims, 35 Drawing Sheets

Related U.S. Application Data

(60) Provisional application No. 62/856,348, filed on Jun. 3, 2019, provisional application No. 62/745,909, filed on Oct. 15, 2018.

(52) U.S. Cl.
CPC ....... *A61M 16/109* (2014.02); *A61M 16/1095* (2014.02); *A61M 2205/3334* (2013.01); *A61M 2205/3365* (2013.01); *A61M 2205/3368* (2013.01); *A61M 2205/3653* (2013.01); *A61M 2205/50* (2013.01); *A61M 2205/8206* (2013.01)

(58) Field of Classification Search
CPC .............. A61M 16/022; A61M 16/024; A61M 16/1075; A61M 16/109; A61M 16/1095; A61M 16/16; A61M 2016/0033; A61M 2205/82; A61M 2205/8206; A61M 2205/8262
See application file for complete search history.

(56) References Cited

U.S. PATENT DOCUMENTS

| | | | |
|---|---|---|---|
| 4,971,049 A | 11/1990 | Rotariu | |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,800,970 B2 | 8/2014 | Heine et al. | |
| 8,844,522 B2 | 9/2014 | Huby et al. | |
| 9,802,022 B2 | 10/2017 | Smith et al. | |
| 11,529,481 B2 * | 12/2022 | Bath | A61M 16/024 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0065054 A1 * | 3/2010 | Bowman | A61M 16/0051 128/204.21 |
| 2011/0162647 A1 * | 7/2011 | Huby | A61M 16/16 128/203.14 |
| 2012/0266880 A1 | 10/2012 | Young et al. | |
| 2014/0366876 A1 | 12/2014 | Huby et al. | |
| 2015/0120067 A1 | 4/2015 | Wing | |
| 2018/0008795 A1 | 1/2018 | Smith et al. | |
| 2019/0117919 A1 | 4/2019 | Panarello | |
| 2021/0008312 A1 * | 1/2021 | Young | G06F 21/6245 |

FOREIGN PATENT DOCUMENTS

| | | | |
|---|---|---|---|
| EP | 2 098 260 A1 | 9/2009 | |
| JP | 2013543753 A | 12/2013 | |
| JP | 7436472 B2 | 1/2022 | |
| WO | WO 98/004310 A1 | 2/1998 | |
| WO | WO 98/034665 A1 | 8/1998 | |
| WO | WO 2000/078381 A1 | 12/2000 | |
| WO | WO 2004/073778 A1 | 9/2004 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/028427 A1 | 3/2010 | |
| WO | WO 2010/135785 A1 | 12/2010 | |
| WO | WO 2012/171072 A1 | 12/2012 | |
| WO | WO 2013/020167 A1 | 2/2013 | |
| WO | WO-2015082970 A1 * | 6/2015 | ......... A61M 16/109 |

OTHER PUBLICATIONS

Internationl Search Report for PCT/IB2019/058743 mailed Dec. 17, 2019.
Written Opinion PCT/IB2019/058743 mailed Dec. 17, 2019.
European Search Report for EP Application No. EP 19 87 4570 issued June 17, 2022.
European Search Report for European Application No. 24175454.8 issued Nov. 4, 2024.

* cited by examiner

SYSTEMS AND METHODS FOR ACTIVE POWER MANAGEMENT IN A MEDICAL DEVICE

1 CROSS-REFERENCE TO RELATED PATENTS AND APPLICATIONS

This application is a continuation of U.S. application Ser. No. 16/600,741, filed Oct. 14, 2019, which claims the benefit of U.S. Provisional Application No. 62/745,909, filed on Oct. 15, 2018, and U.S. Provisional Application No. 62/856,348, filed on Jun. 3, 2019, each of which is incorporated herein by reference in its entirety.

This application is related to the following commonly-assigned US patents and patent applications, the entire contents of each of which are incorporated by reference: U.S. patent application Ser. No. 14/472,651 titled "Power Management in Respiratory Treatment Apparatus"; U.S. patent application Ser. No. 15/710,879 titled "Humidification of Respiratory Gases"; U.S. Pat. No. 8,844,522 "Power Management in Respiratory Treatment Apparatus"; and U.S. Pat. No. 9,802,022 titled "Humidification of Respiratory Gases".

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use. More particularly, the technology described herein relates to power management in medical devices or apparatus.

2.2 Background of the Technology

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

One of the design choices for the device includes a type of power supply included in the device. The power supply type may determine the amount of power that is available for components of device, the weight and size of the device, and cost. While smaller and lighter devices are desired, reduction in the size of power supply will also reduce the amount of available power. In other situations, the type of power that can be used in a device may already be determined but it may be desirable to include additional subsystem components. The subsystem components may include, for example, a blower, a heater plate, a heated tube or other components (e.g., a communication module). These additional subsystem components may need to use the limited power that is provided by the power supply already included in the device. Accordingly, it is desirable to provide for efficient power management of a power supply included in devices, and particularly in devices in which the power supply may not have enough power to simultaneously power all of the device components and subsystem components.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises providing adaptive power managements in a respiratory treatment apparatus.

Another aspect of one form of the present technology comprises providing adaptive power managements in a respiratory treatment apparatus providing a flow of pressurized gas that may be heated and/or humidified.

One form of the present technology comprises providing adaptive power managements of multiple components included in medical devices such as devices used in the screening, diagnosis, monitoring, amelioration, treatment or prevention of a respiratory disorder An aspect of one form of the present technology is a portable RPT device that may be carried by a person, e.g., around the home of the person.

Another aspect of the present technology is directed to a respiratory treatment apparatus comprising: a power supply; a pressure generator configured to generate a flow of air; a heating element configured to heat the generated flow of air; one or more sensors configured to generate sensor signals representing a property of the flow of air; and a processing system. The processing system may be configured to: receive the sensor signals; based on the received sensor signals, determine a control signal for controlling the heating element; receive signals corresponding to current drawn by the pressure generator; receive signals corresponding to current drawn by the heating element; based on (1) the signals corresponding to current drawn by the pressure generator, (2) the signals corresponding to current drawn by the heating element, (3) the determined control signal for the heating element, and (4) power of the power supply, generate a new control signal for controlling the heating element; and control operation of the heating element using the new control signal for controlling the heating element.

In examples, (a) the power that could be drawn by the pressure generator and the heating element combined exceeds the capability of the power supply, (b) when a sum of current drawn by the pressure generator and current that would be drawn by the heating element using the determined control signal for the heating element exceeds a maximum current of the power supply, generate the new control signal such that the new control signal will cause the heating element to draw less current than the current that would be drawn with the determined control signal, (c) when a sum of current drawn by the pressure generator and current that would be drawn by the heating element using the determined control signal for the heating element does not exceed a maximum current of the power supply, generate the new control signal such that the new control signal will cause the heating element to draw more current than the current that would be drawn with the determined control signal, (d) at least one of the one or more sensors is configured to generate sensor signals representing temperature of the air flow and the processing system is further configured to control the pressure generator based on the sensor signals representing temperature of the flow of air, (e) at least one of the one or more sensors is a pressure sensor configured to generate sensor signals representing pressure of the air flow and the control signal for controlling the heating element is determined based on the sensor signals representing pressure of the flow of air, (f) at least one of the one or more sensors is a flow sensor configured to generate sensor signals representing flow of the air flow and the processing system is configured to control the pressure generator based on the sensor signals representing flow of the flow of air and the control signal for controlling the heating element is determined based on the sensor signals representing flow of the flow of air, (g) the flow of air may be delivered to a patient interface via a tube (e.g., flexible tube) coupled to the flow generator, (h) the generated control signal for controlling the heating element is controlled to accrue a heat deficit in a time period and return the accrued heat deficit in a subsequent time period, (i) the generated control signal for controlling the heating element decreases the heat produced by the heating element during a first period and increases the heat produced by the heating element during a second period followed by the first period, and/or (j) during the first period the power of the power supply is lower than the power consumed by the pressure generator and the heating elements and/or during the second period the power of the power supply exceeds the power consumed by the pressure generator and the heating elements.

Another aspect of the present technology is directed to an apparatus for treating a respiratory disorder in a patient, the apparatus comprising: a power supply; a pressure generator configured to generate a flow of breathable gas for treating the respiratory disorder; a humidifier configured to store a supply of water to humidify the breathable gas and comprising a first heating element configured to heat the supply of water; a second heating element configured to heat the humidified breathable gas in a hose configured to deliver the humidified breathable gas to the patient; a transducer configured to generate a flow signal representing a property of the flow of breathable gas; and a controller. The controller may be configured to: based on the flow signal, determine a first control signal for controlling the first heating element, and a second control signal for controlling the second heating element; based on (1) measured current drawn by the pressure generator during operation of the pressure generator, (2) the first control signal, and (3) the second control signal, determine if power to be used by the apparatus exceeds a peak power of the power supply; if it is determined that the power to be used by the apparatus exceeds the peak power of the power supply, modify the first control signal and/or the second control signal to decrease the power used by the first heating element and/or the second heating element; and if it is determined that the power to be used by the apparatus does not exceed the peak power of the power supply, modify the first control signal and/or the second control signal to increase the power used by the first heating element and/or the second heating element.

In examples, (a) the first and second control signals are pulse width modulated signals, (b) the first control signal is a first pulse width modulated signal and the second control signal is a second pulse width modulated signal that is offset in time from the first pulse width modulated control signal, (c) if it is determined that the power to be used by the apparatus does not exceed the peak power of the power supply, the first control signal and the second control signal are modified to increase the power used by the first heating element and the second heating element with priority given to the second heating element, (d) if it is determined that the power to be used by the apparatus exceeds the peak power of the power supply, modify the first control signal and the second control signal to decrease the power used by the first heating element and/or the second heating element with priority given to the second heating element, (e) the first control signal is a first current set point provided to a proportional, proportional-differential, or proportional-integral controller configured to control operation of the second heating element, and the second control signal is a second current set point provided to a proportional, proportional-differential, or proportional-integral controller configured to control operation of the second heating element, (d) determining if power to be used by the apparatus exceeds a peak power of the power supply includes determining whether a sum of (1) a current drawn by the apparatus without the current drawn by the first and second heating elements, (2) a current that would be drawn by the first heating element using the determined first control signal, and (3) a current that would be drawn by the second heating element using the determined second control signal, is greater than a maximum current that can be provided by the power supply, (e) the flow signal corresponds to a patient's respiratory cycle during use of the apparatus and the first control signal and the second control signal are determined to control offsetting peak power operation of the first heating element and the second heating element based on the flow signal, (f) the power of the power supply is lower than the power simultaneously drawn by the pressure generator, the first heating element, and the second heating element, and/or (g) the humidified breathable gas in the hose is delivered to the patient via a patient interface coupled to the hose.

Another aspect of the present technology is directed to a respiratory treatment device comprising: a flow generator configured to provide a flow of breathable gas to a patient; an accessory apparatus including a tube heater and a humidifier heater; a power supply; and a controller coupled to the flow generator, the accessory apparatus, and the power supply. The controller may be configured to: control operations of the flow generator, delivery tube heater, and the humidifier heater; determine a first pulse width modulated control signal for controlling the delivery tube heater and a second pulse width modulated control signal for controlling the humidifier heater; and upon determining that a current rating of the power supply does not exceed a current that will be drawn by the flow generator, the delivery tube heater when the determined first pulse width modulated control signal will be applied to the delivery tube heater, and the humidifier heater when the determined second pulse width modulated control signal will be applied to the humidifier heater, increasing a duty cycle of the first pulse width modulated control signal and the second pulse width modulated control signal.

In examples, (a) the controller is further configured to upon determining that the current rating of the power supply exceeds a current that will be drawn by the flow generator, the delivery tube heater when the determined first pulse width modulated control signal will be applied to the delivery tube heater, and the humidifier heater when the determined second pulse width modulated control signal will be applied to the humidifier heater, reducing the duty cycle of the first pulse width modulated control signal and the second pulse width modulated control signal, (b) the first pulse width modulated control signal is offset in time from the second pulse width modulated control signal, and/or (c) the flow generator is coupled to a patient interface via a tube to provide the flow of breathable gas to a patient.

Another aspect of the present technology is directed to a respiratory treatment device comprising: a flow generator configured to provide a flow of breathable gas to a patient; an accessory apparatus including a tube heater and a humidifier heater; a power supply; and a controller coupled to the flow generator, the accessory apparatus, and the power supply. The controller may be configured to: control operations of the flow generator, delivery tube heater, and the humidifier heater; determine a first pulse width modulated control signal for controlling the delivery tube heater and a second pulse width modulated control signal for controlling the humidifier heater; and upon determining that a current rating of the power supply does not exceed a current that will be drawn by the flow generator, the delivery tube heater when the determined first pulse width modulated control signal will be applied to the delivery tube heater, and the humidifier heater when the determined second pulse width modulated control signal will be applied to the humidifier heater, increasing a duty cycle of the first pulse width modulated control signal and the second pulse width modulated control signal.

In examples, (a) the controller is further configured to upon determining that the current rating of the power supply exceeds a current that will be drawn by the flow generator, the delivery tube heater when the determined first pulse width modulated control signal will be applied to the delivery tube heater, and the humidifier heater when the determined second pulse width modulated control signal will be applied to the humidifier heater, reducing the duty cycle of the first pulse width modulated control signal and the second pulse width modulated control signal, and/or (b) the first pulse width modulated control signal is offset in time from the second pulse width modulated control signal, and/or (c) the flow generator is coupled to a patient interface via a tube to provide the flow of breathable gas to a patient.

Another aspect of the present technology is directed to a method of operating a respiratory treatment apparatus for generating a flow of breathable gas in order to treat a respiratory disorder, the method comprising: measuring a property of the flow of air, using a transducer; determining, by a controller and based on the measured property, a first control signal for controlling a pressure generator configured to generate a flow of breathable gas for treating the respiratory disorder, a second control signal for controlling a first heating element disposed in a humidifier configured to store a supply of water to humidify the breathable gas, and a third control signal for controlling a second heating element configured to heat the humidified breathable gas in a hose configured to deliver the humidified breathable gas to a patient; determining, by the controller and based on (1)

measured current drawn by the pressure generator during control of the pressure generator using the first control signal, (2) the second control signal, and (3) the third control signal, if power to be used by the respiratory treatment apparatus exceeds a peak power of a power supply used to power the respiratory treatment apparatus; if it is determined that the power to be used by the respiratory treatment apparatus exceeds the peak power of the power supply, modifying, by the controller, the second control signal and/or the third control signal to decrease the power used by the first heating element and/or the second heating element; and if it is determined that the power to be used by the respiratory treatment apparatus does not exceed the peak power of the power supply, modifying, by the controller, the second control signal and/or the third control signal to increase the power used by the first heating element and/or the second heating element.

Another aspect of the present technology is directed to a non-transitory storage medium having stored therein an information processing program for controlling operation of a respiratory treatment apparatus configured to generate a flow of breathable gas in order to treat a respiratory disorder, the program, when executed, causing respiratory treatment apparatus to: receive a property of the flow of breathable gas from a transducer; determine, based on the property of the flow of breathable gas, a first control signal for controlling a pressure generator configured to generate the flow of breathable gas, a second control signal for controlling a first heating element disposed in a humidifier configured to store a supply of water to humidify the breathable gas, and a third control signals for controlling a second heating element configured to heat the humidified breathable gas in a hose configured to deliver the humidified breathable gas to a patient; determining, based on (1) measured current drawn by the pressure generator during control of the pressure generator using the first control signal, (2) the second control signal, and (3) the third control signal, if power to be used by the respiratory treatment apparatus exceeds the peak power of a power supply used to power the respiratory treatment apparatus; if it is determined that the power to be used by the respiratory treatment apparatus exceeds peak power of the power supply, modifying the second control signal and/or the third control signal to decrease the power used by the first heating element and/or the second heating element; and if it is determined that the power to be used by the apparatus does not exceed the peak power of the power supply, modifying the second control signal and/or the third control signal to increase the power used by the first heating element and/or the second heating element.

Another aspect of the present technology is directed to a respiratory treatment device comprising: a power supply; a flow generator configured to provide a flow of breathable gas to a patient; one or more heating elements; a processing system including at least one processor, the processing system configured to determine heating control signals for controlling the one or more heating elements and flow control signals for controlling the flow generator; and hardware circuitry. The hardware circuitry may be configured to: receive heating control signals for controlling the one or more heating elements; based on operation of the flow generator and the one or more heating elements, determine a power consumption signal representing total power consumption; and based on the power consumption signal, output modified heating control signals for controlling the one or more heating elements.

In examples, (a) the hardware circuity is configured to output the received heating control signals for controlling the one or more heating elements without modification when the power consumption signal is above a predetermined value, and output the modified heating control signals for controlling the one or more heating elements when the power consumption signal is below the predetermined value, (b) the hardware circuity is configured to generate, based on the power consumption signal, a pulse width modulated power signal, and the modified heating control signals are generated by combining the pulse width modulated power signal with the received heating control signals, (c) the hardware circuity is configured to generate, based on the power consumption signal, a pulse width modulated power signal and includes a logic gate, for each of the received heating control signals, configured to generate the modified heating control signals by combining the respective received heating control signal with the pulse width modulated power signal, (d) the hardware circuity is further configured to: receive flow generator current signal and current signals for one or more heating elements, and wherein the power consumption signal is determined by summing voltages representing the received flow generator current signal and voltages representing the received current signals for one or more heating elements, and/or (e) at least one of the heating elements is provided in a tube heater and at least one of the heating elements is provided in a humidifier heater.

Another aspect of the present technology is directed to a respiratory treatment device comprising: a power supply; a flow generator configured to provide a flow of breathable gas to a patient; one or more heating elements; hardware circuitry; and a processing system including at least one processor. The hardware circuitry may be configured to: receive flow generator current signal representing current drawn by the flow generator and current signals for one or more heating elements representing the current drawn by the one or more heating elements, and determine a power consumption signal by summing a voltage representing the received flow generator current signal and voltages representing the received current signals for one or more heating elements. The processing system may be configured to: receive, from the hardware circuitry, the power consumption signal; determine flow control signals for controlling the flow generator; and determine, based on the power consumption signal, heating control signals for controlling the one or more heating elements.

In examples, (a) determining the heating control signals includes: determining pulse width modulated control signals for each of the heating elements; when the received power consumption signal is above a predetermined limit, transmit the determined pulse width modulated control signals to each respective heating element; and when the received power consumption signal is below the predetermine limit, modify each of the determined pulse width modulated control signals and transmit the modified pulse width modulated control signals to each respective heating element, and/or (b) the hardware circuitry is configured to buffer and amplify the received flow generator current signal; and the power consumption signal is a low pass filtered sum of the voltage representing the received flow generator current signal and the voltages representing the received current signals for one or more heating elements.

Another aspect of the present technology is directed to a respiratory treatment apparatus comprising: a power supply; a pressure generator configured to generate a flow of air; a heating element configured to heat the generated flow of air; one or more sensors configured to generate sensor signals representing a property of the flow of air; and a processing system configured to: generate a control signal for the heating element, wherein the heating element is controlled to accrue a heat deficit in a time period and return the accrued heat deficit in a subsequent time period.

Another aspect of the present technology is directed to a respiratory treatment apparatus comprising: a power supply; a pressure generator configured to generate a flow of air; a heating element configured to heat the generated flow of air; one or more sensors configured to generate sensor signals representing a property of the flow of air; and a processing system configured to: receive the sensor signals; based on the received sensor signals, determine a control signal for controlling the heating element; receive signals corresponding to current drawn by the pressure generator; receive signals corresponding to current drawn by the heating element; control the heating element based on the signals corresponding to current drawn by the pressure generator, the signals corresponding to current drawn by the heating element, the determined control signal for the heating element, and power of the power supply, wherein the heating element is controlled to accrue a heat deficit in a time period and return the accrued heat deficit in a subsequent time period.

In examples, the flow of breathable gas is delivered to a patent via a tube coupled between a patient interface and a flow generator and/or a humidifier.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 2 shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 3 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.3 Humidifier

Figure 1:
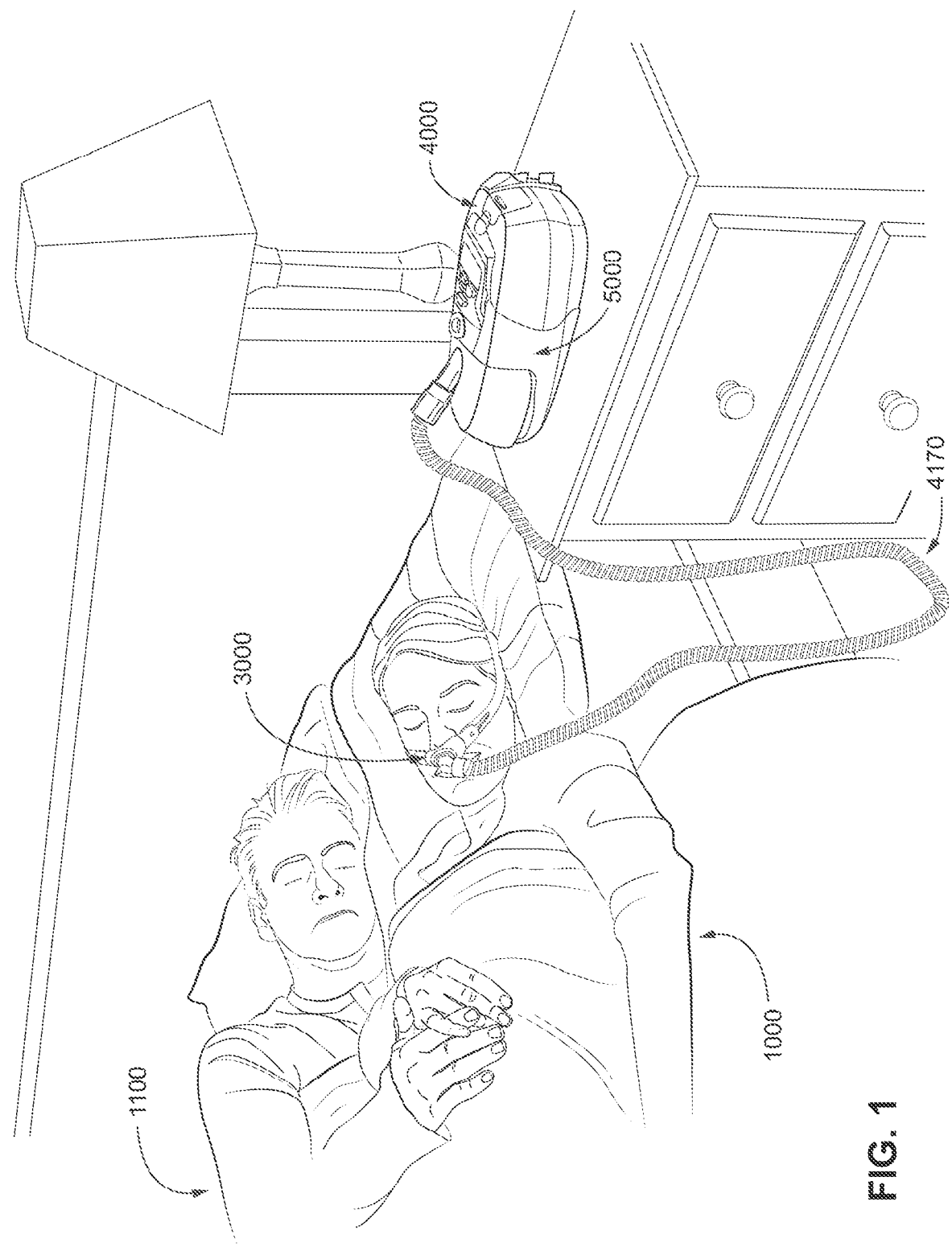
Figure 2:
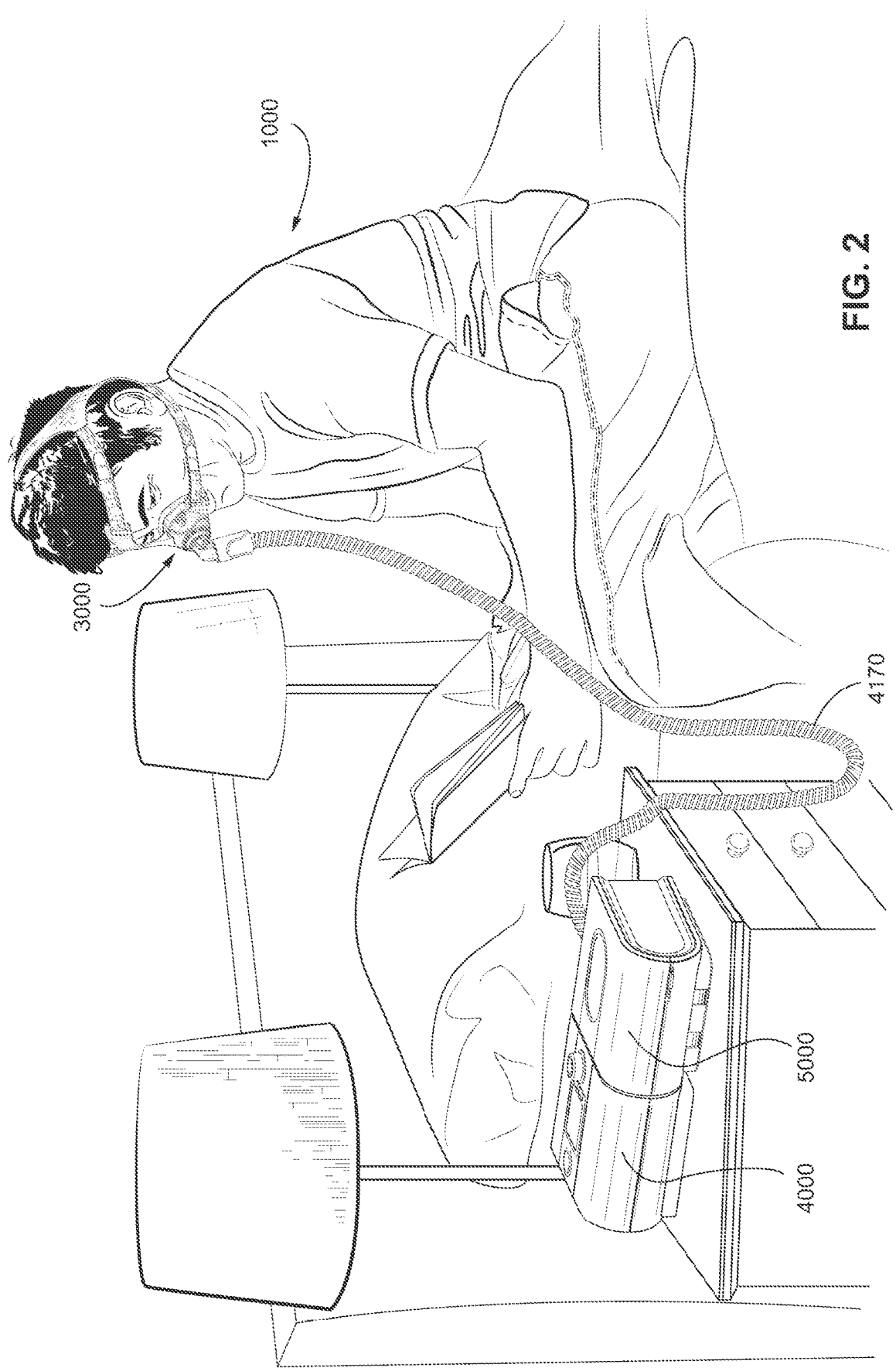
Figure 3:
Figure 4A:
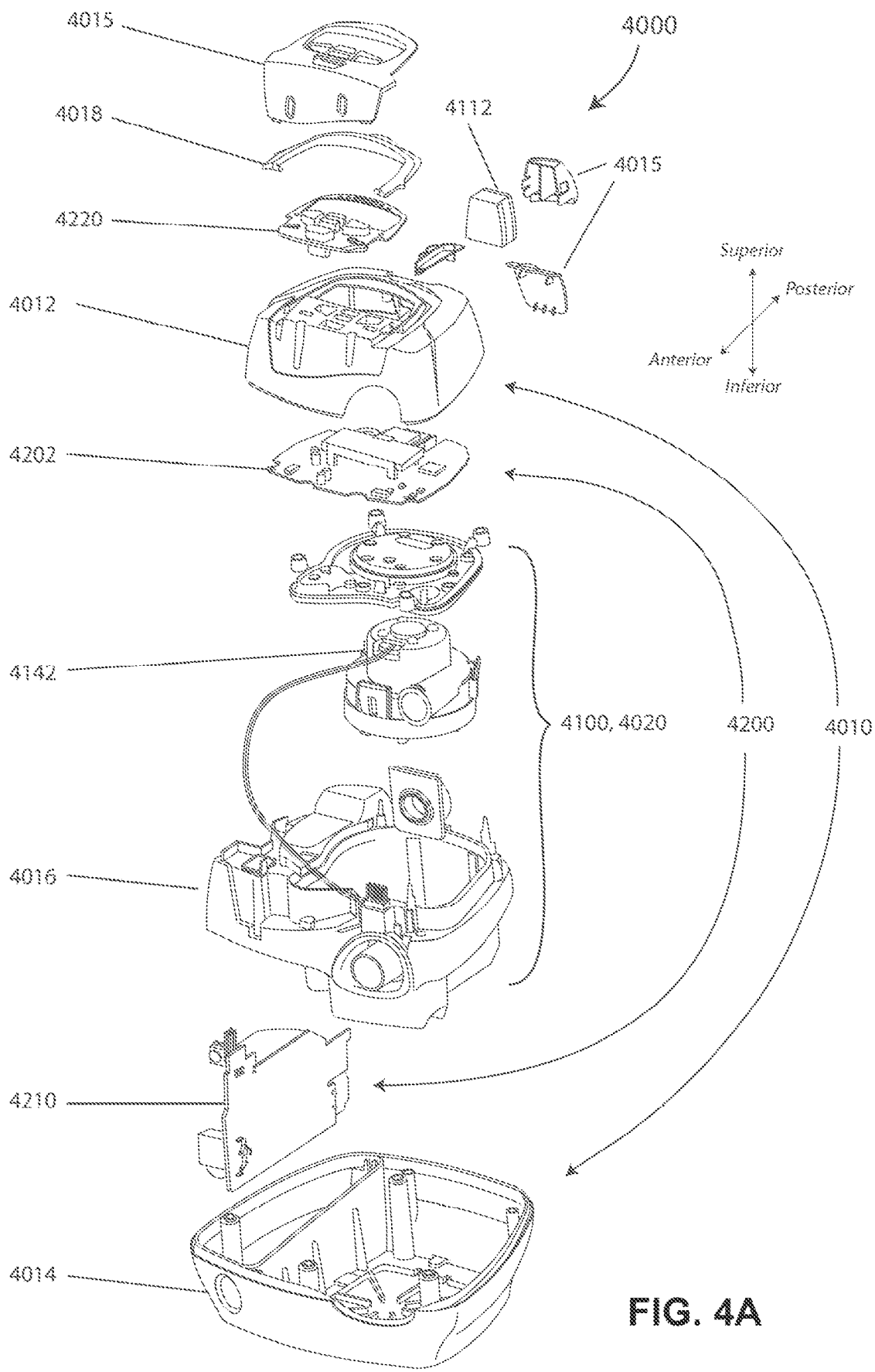
FIG. 4C is a schematic diagram of the electrical components of an RPT device in accordance with one form of the present technology.
FIG. 4D is a schematic diagram of the algorithms implemented in an RPT device in accordance with one form of the present technology.
FIG. 4E is a flow chart illustrating a method carried out by the therapy engine module of FIG. 4D in accordance with one form of the present technology.
Figure 4B:
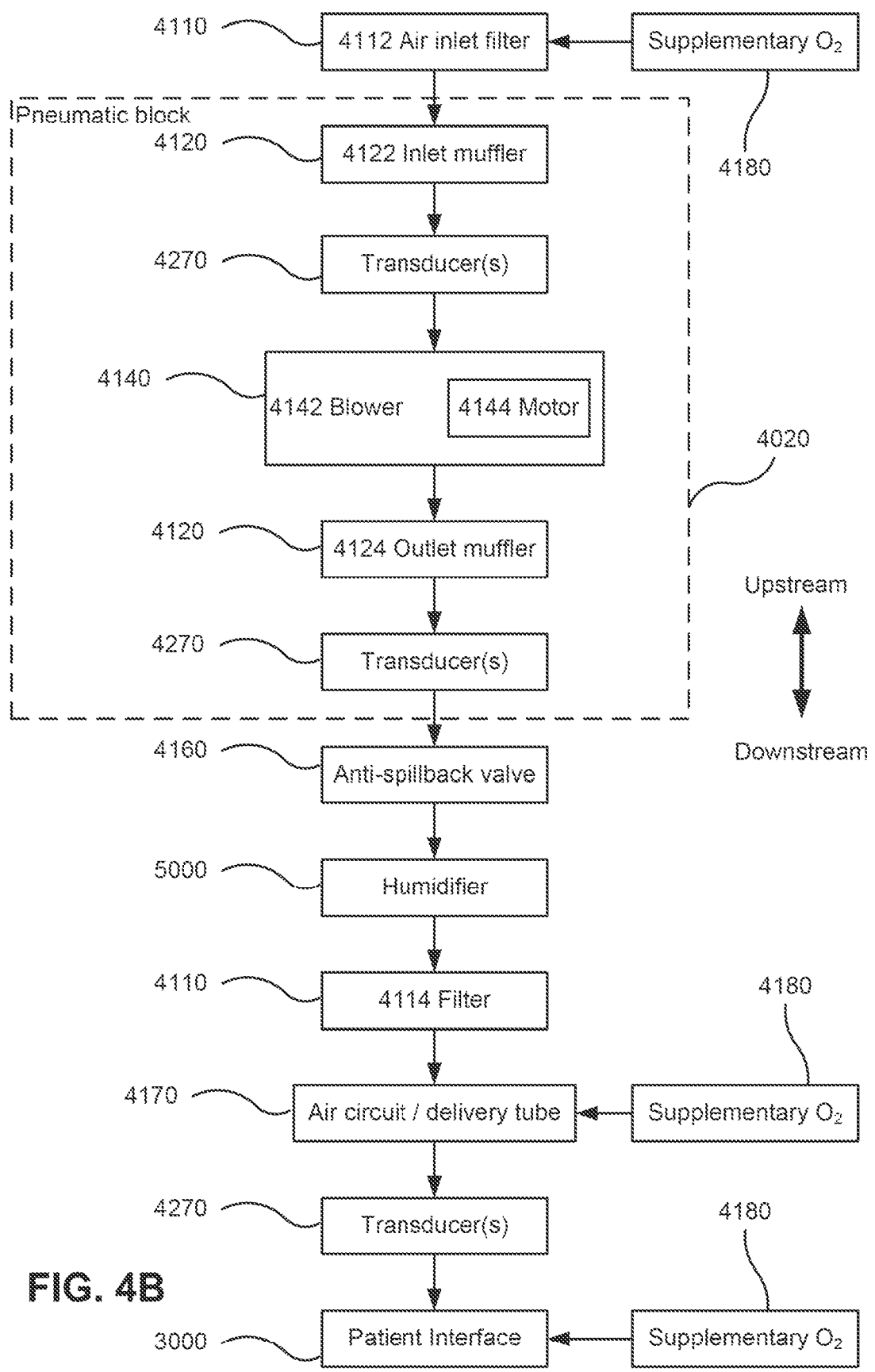
Figure 4C:
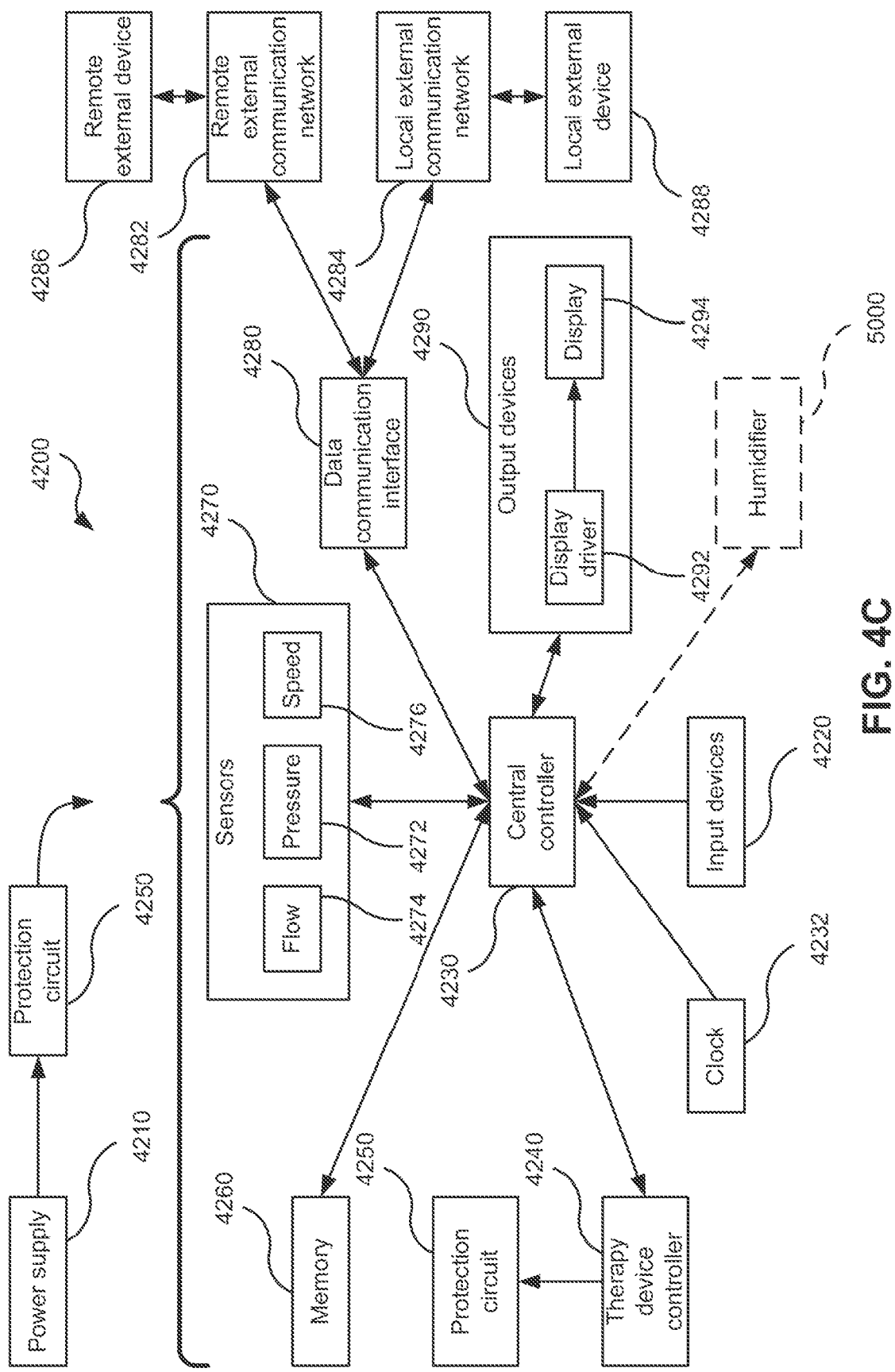
Figure 4D:
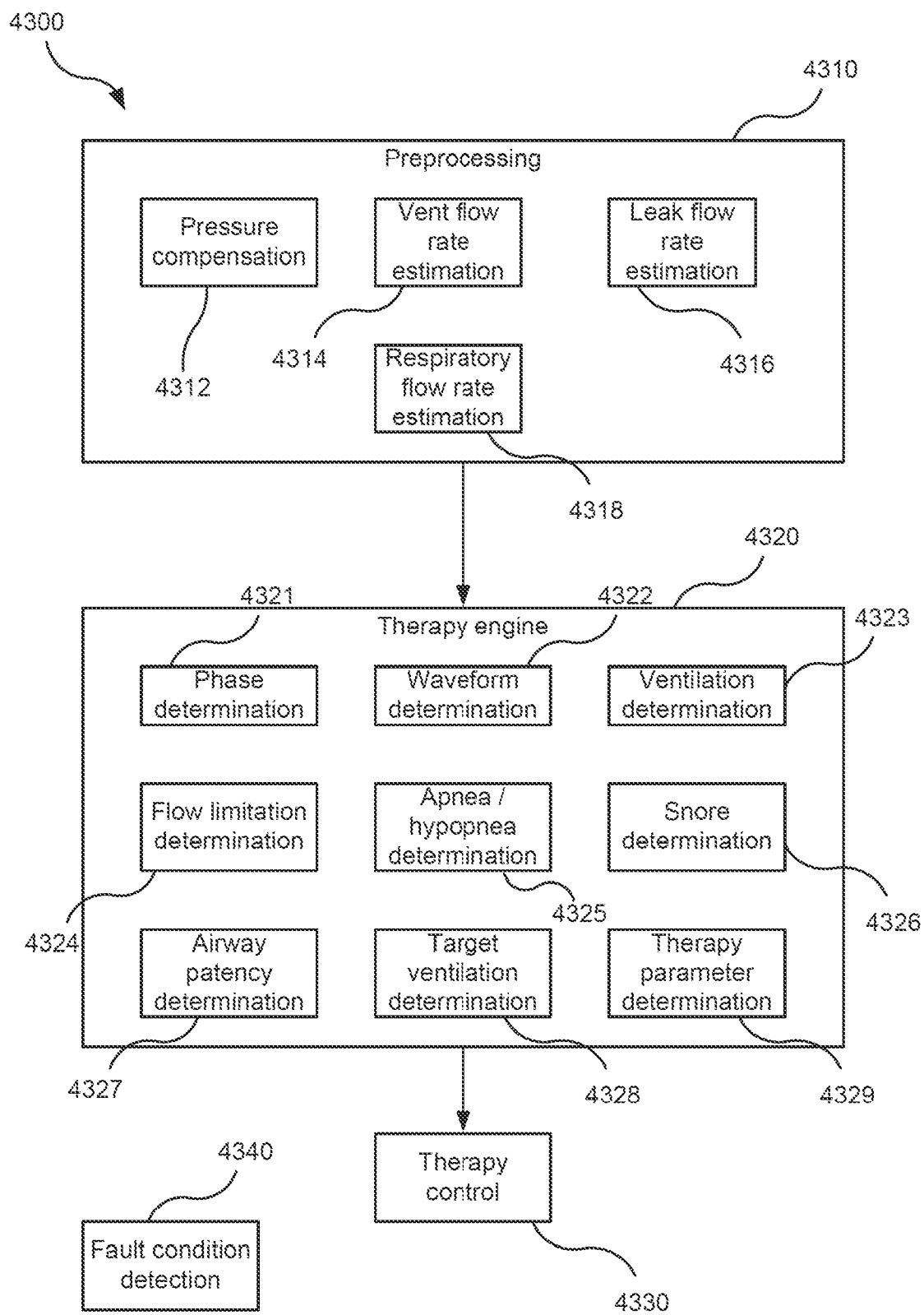
Figure 4E:
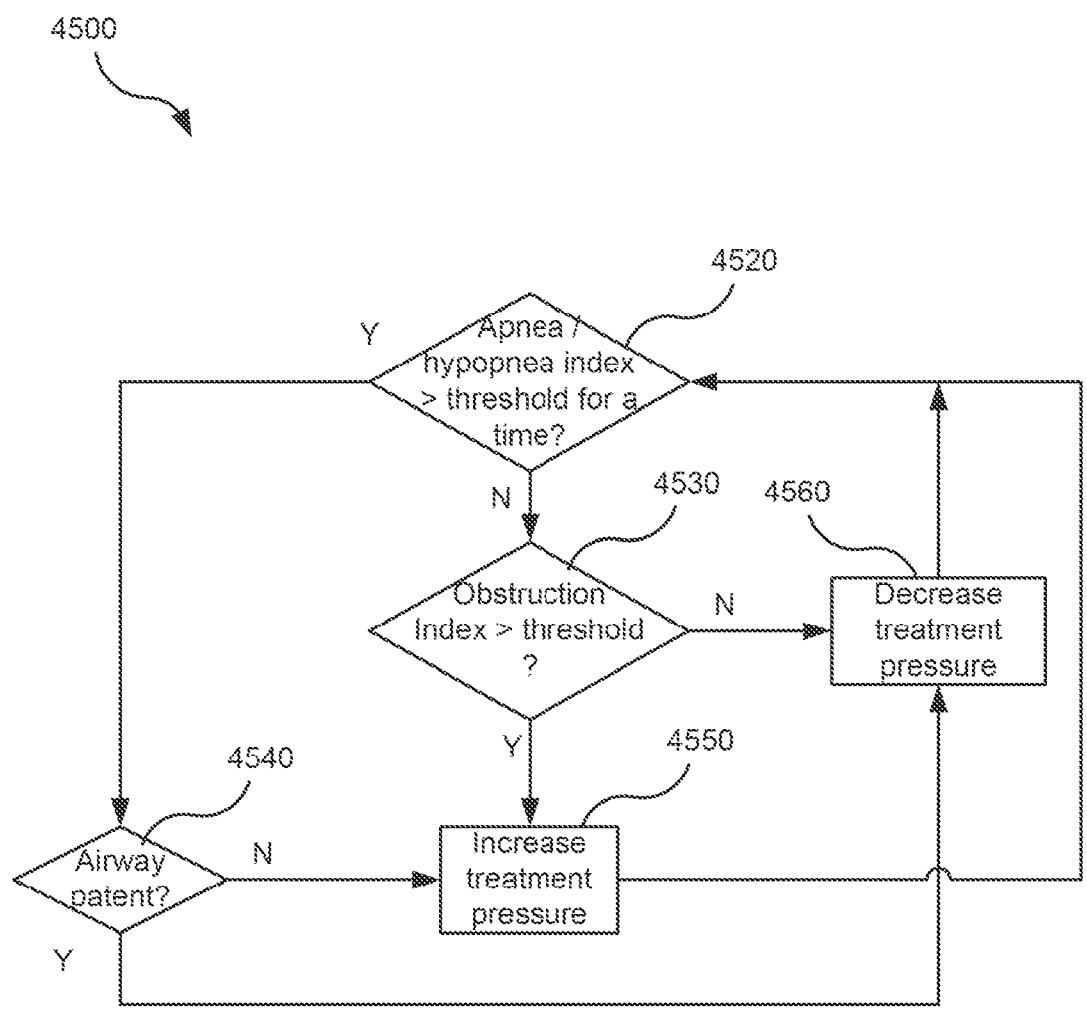
Figure 5A:
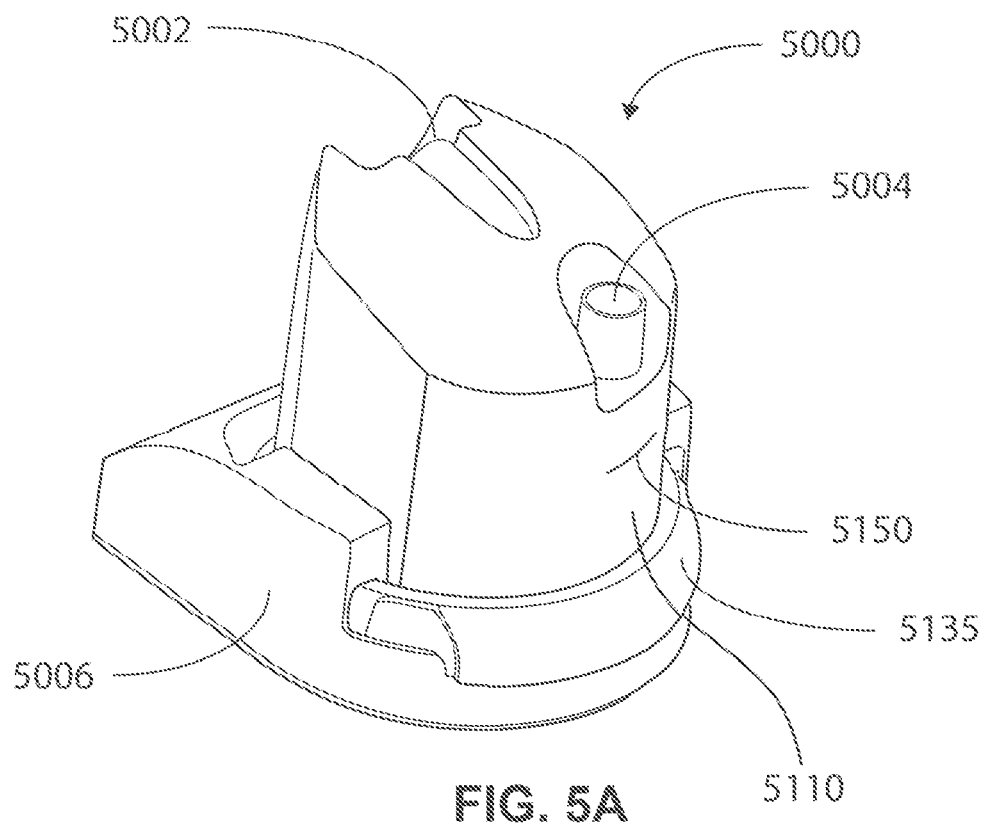

FIG. 5A shows an isometric view of a humidifier in accordance with one form of the present technology.

Figure 5B:
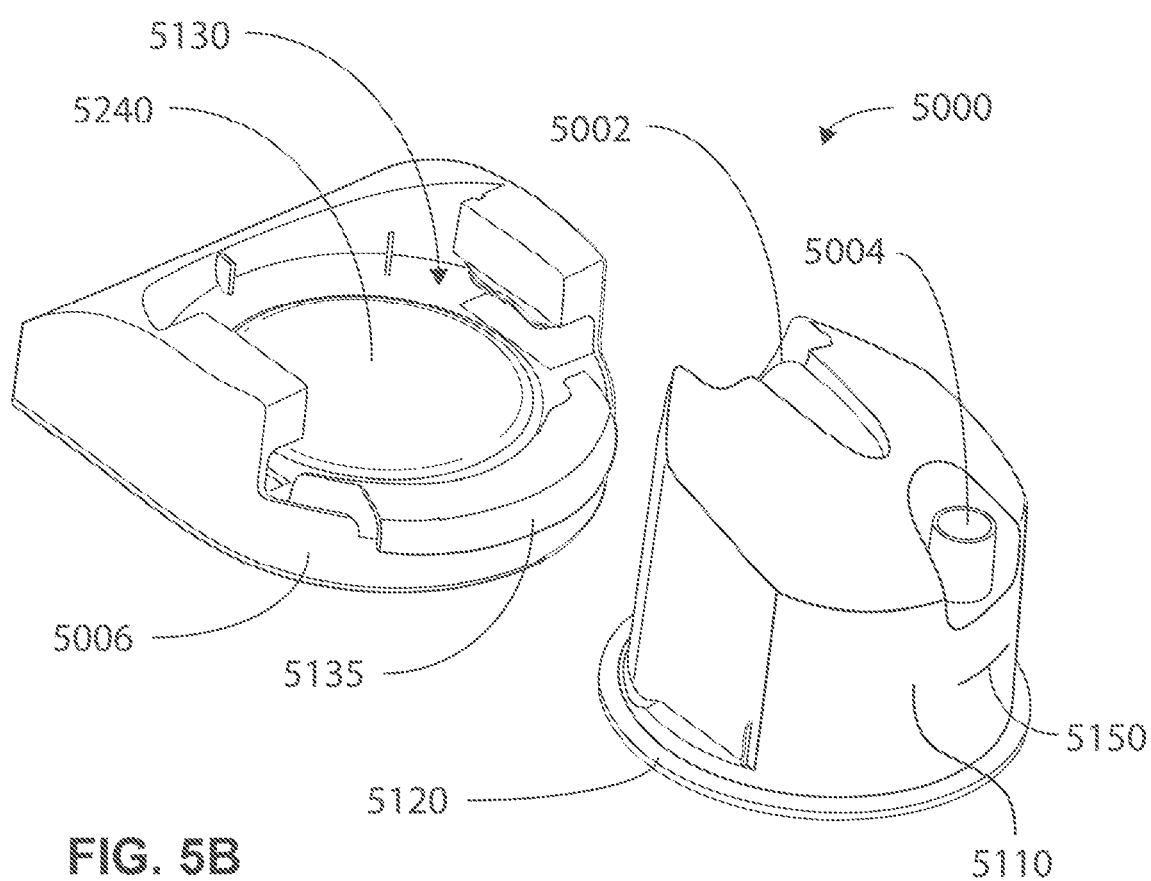

FIG. 5B shows an isometric view of a humidifier in accordance with one form of the present technology, showing a humidifier reservoir 5110 removed from the humidifier reservoir dock 5130.

Figure 5C:
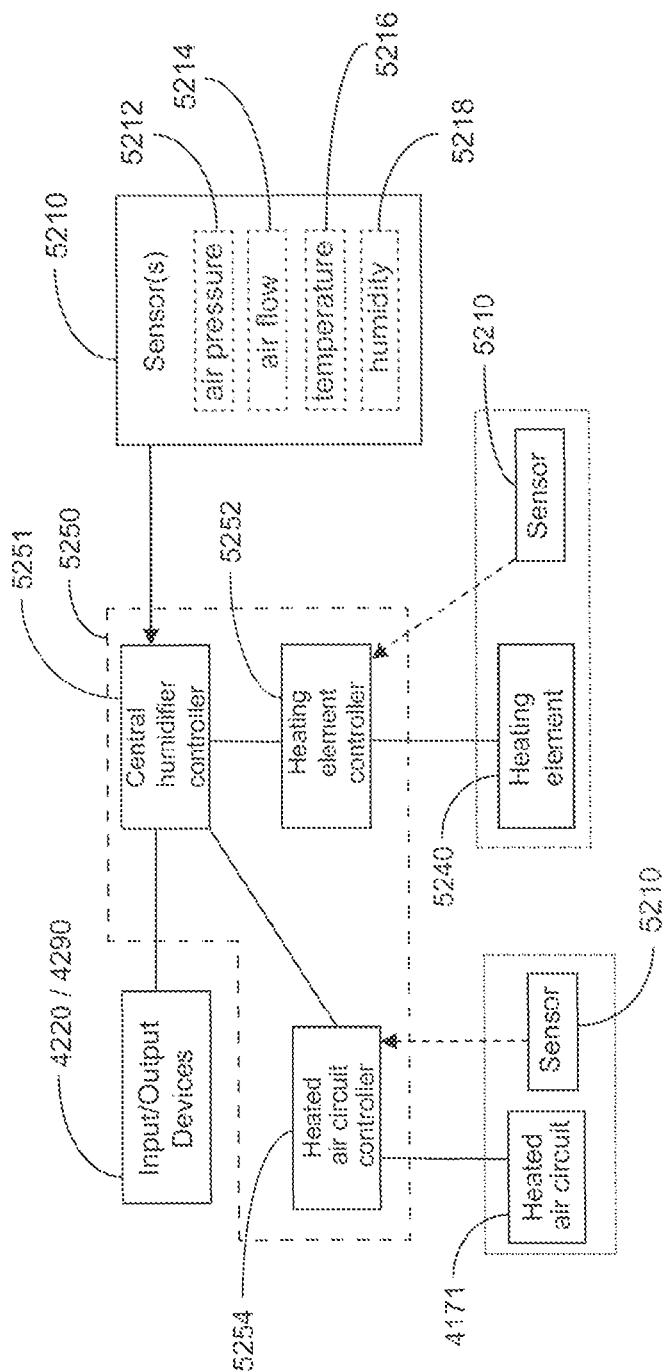

FIG. 5C shows a schematic of a humidifier in accordance with one form of the present technology.

4.4 Active Power Management

Figure 5D:
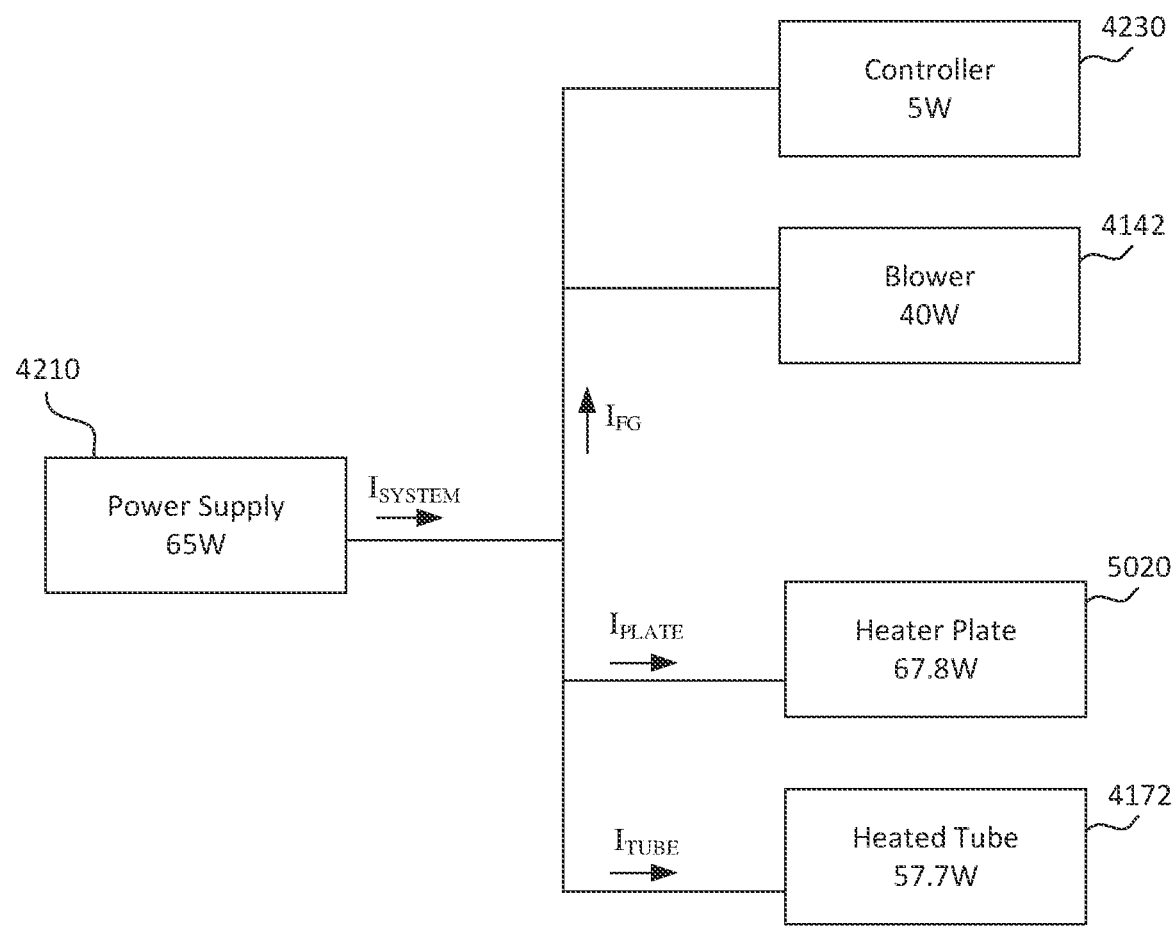

FIG. 5D shows an exemplary architecture of devices using power supplied by the power supply 4210.

Figure 5E:
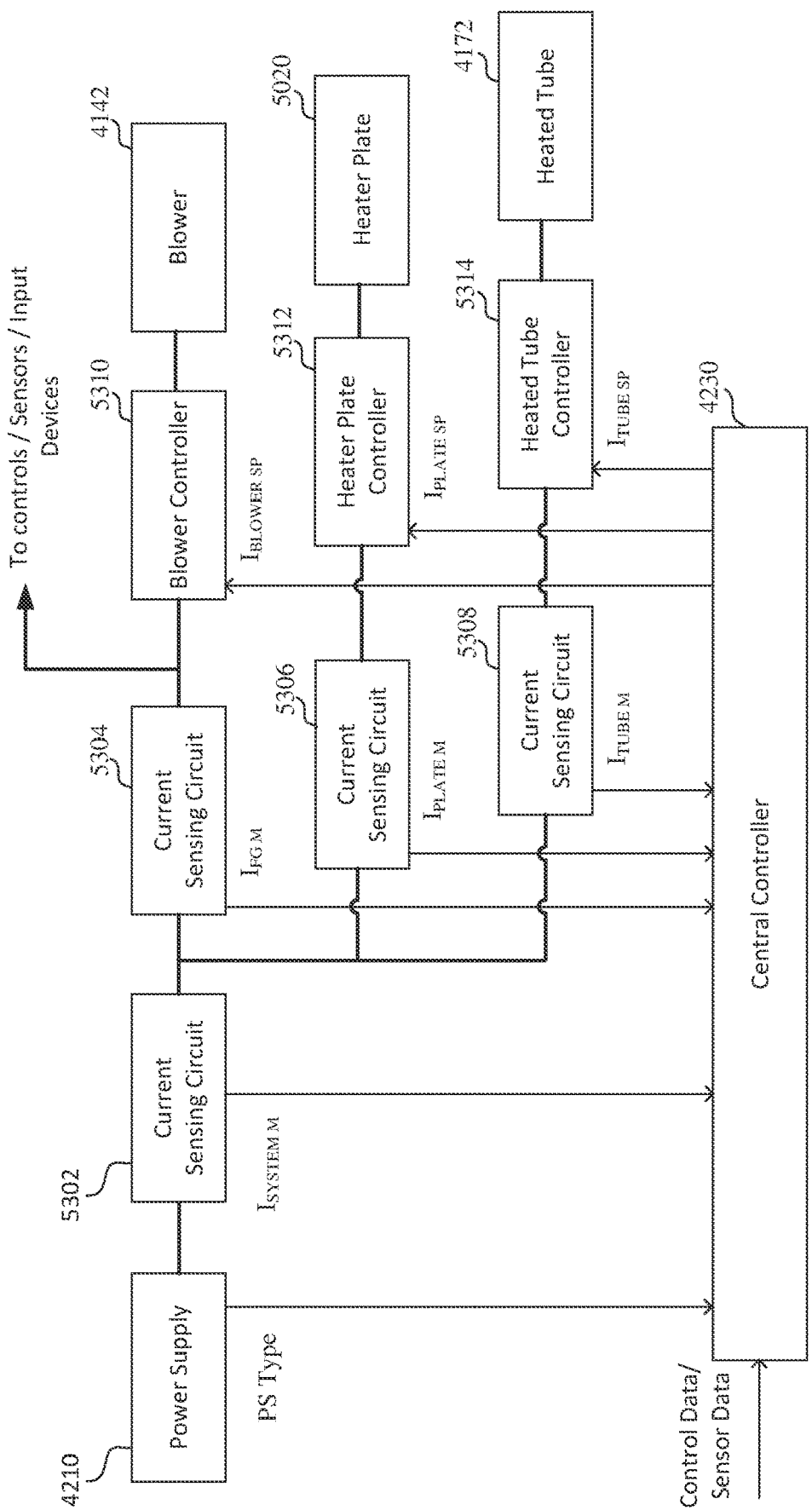

FIG. 5E shows an exemplary architecture for controlling operation of multiple devices using power supplied by power supply 4210.

Figure 5F:
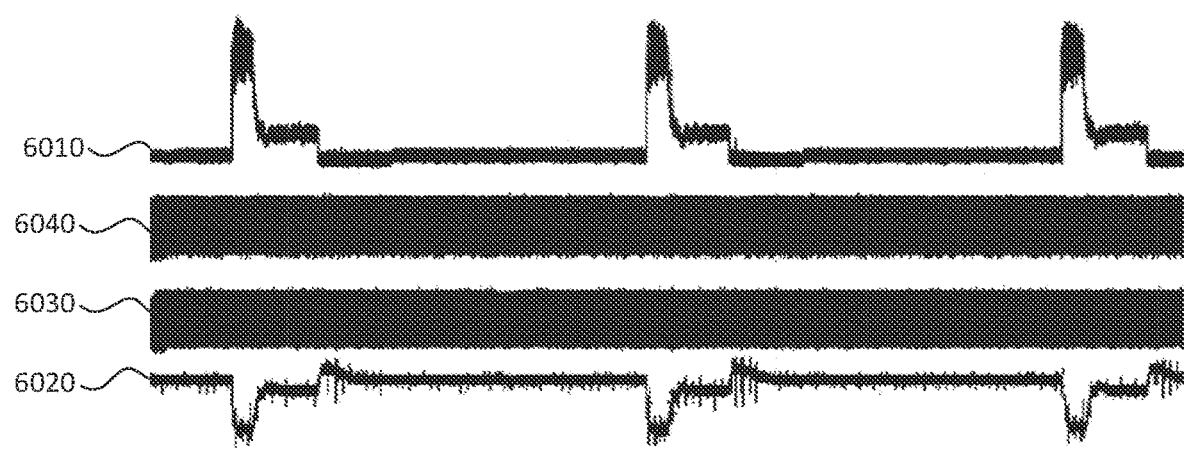
Figure 5G:
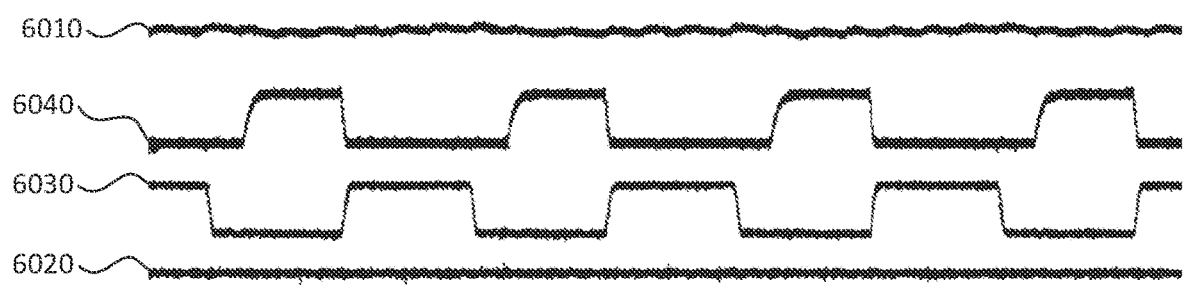

FIGS. 5F and 5G illustrate exemplary power measurements of components in the RPT device 4000.

Figure 5H:
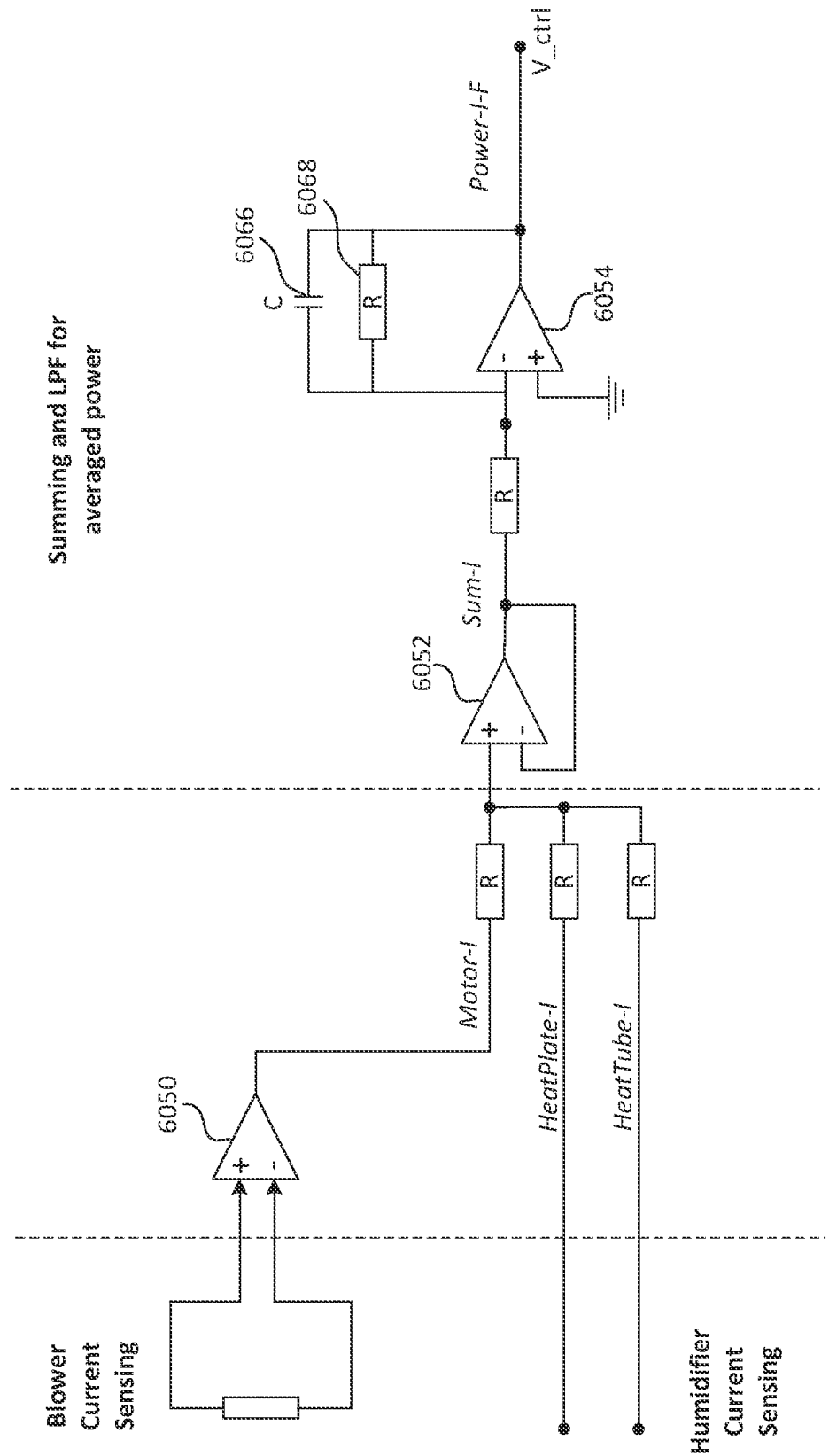

FIG. 5H shows example circuitry that may be used for measuring power used by the RPT device 4000 in one form of the present technology.

Figure 5I:
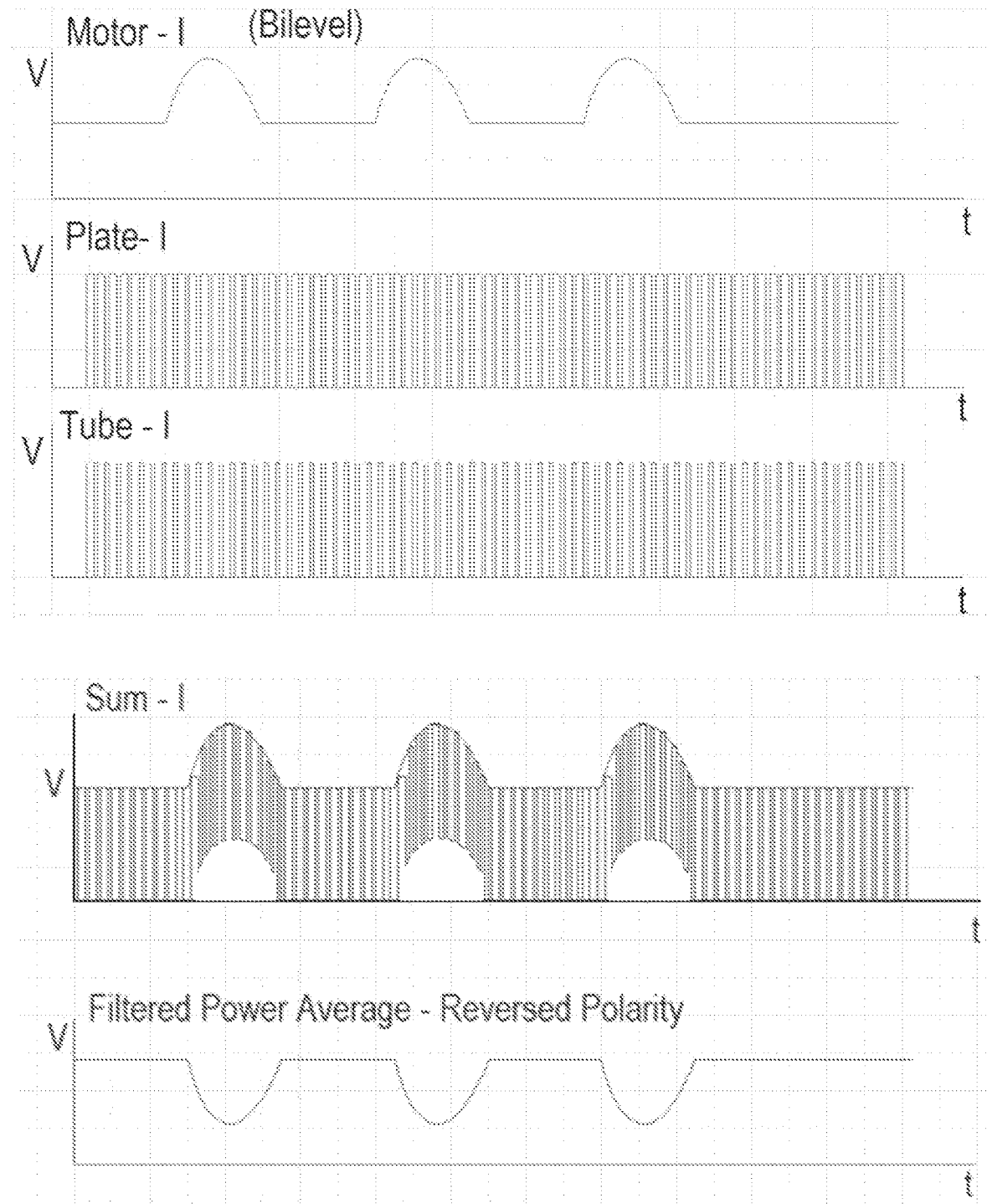

FIG. 5I shows exemplary signal waveforms for circuitry shown in FIG. 5H.

Figure 5J:
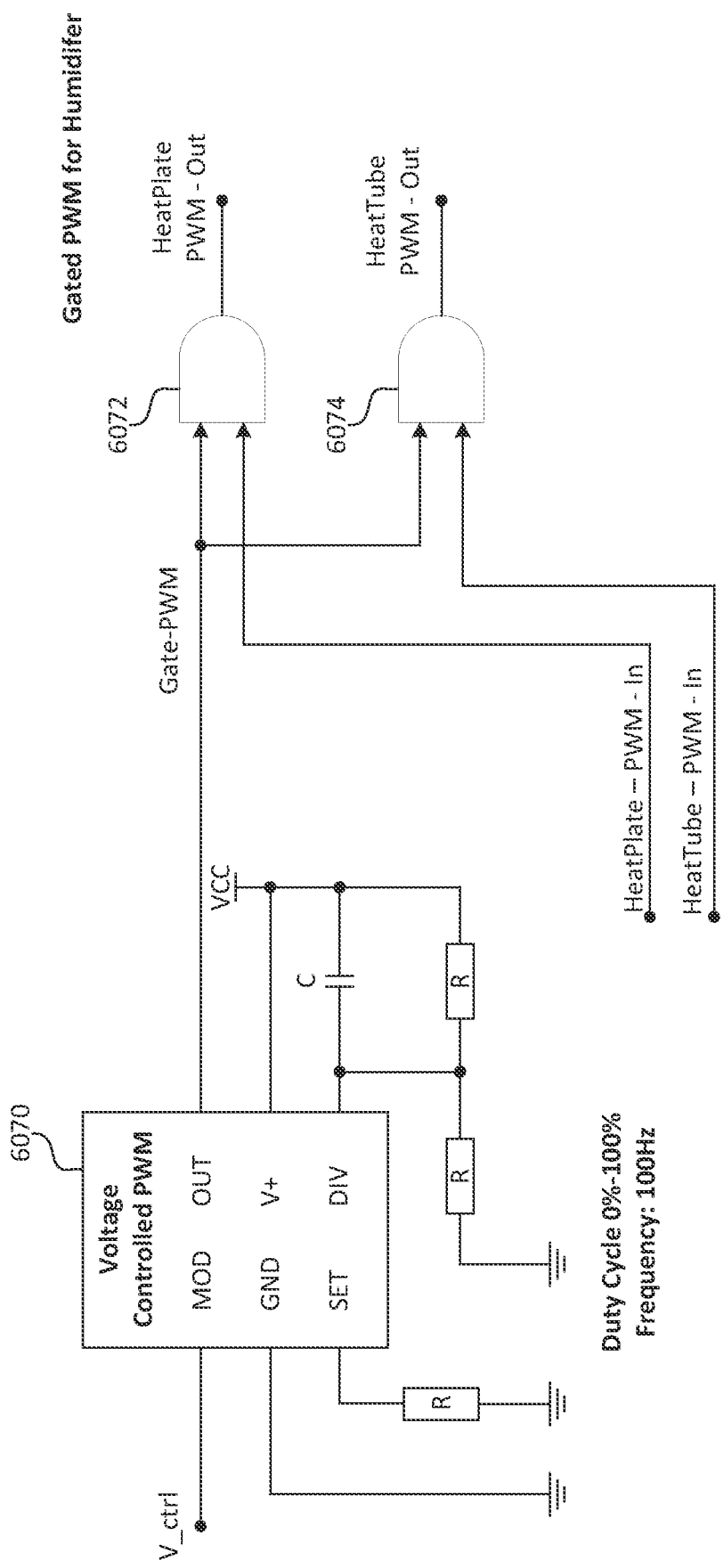

FIG. 5J shows power control circuitry that may be used for controlling operation of the heating elements based on a control signal representing power consumption of the RPT device 4000 in accordance with one form of the present technology.

Figure 5K:
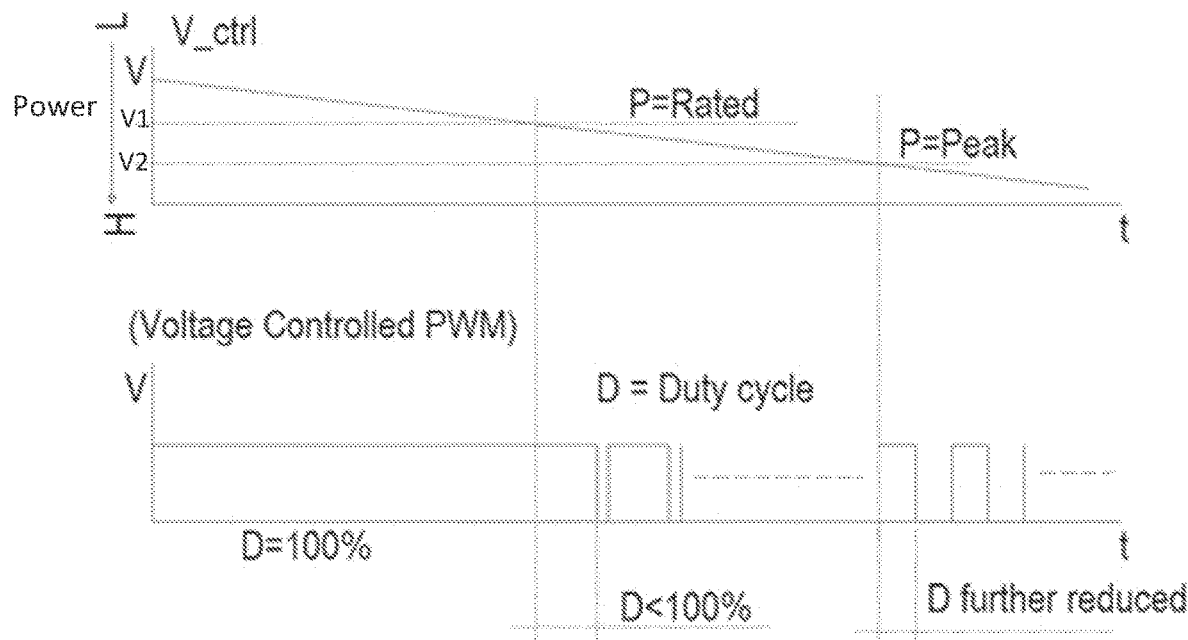

FIG. 5K illustrates output signal Gate-PWM duty cycle being proportional to the control signal control signal V_ctrl in accordance with one form of the present technology.

Figure 5L:
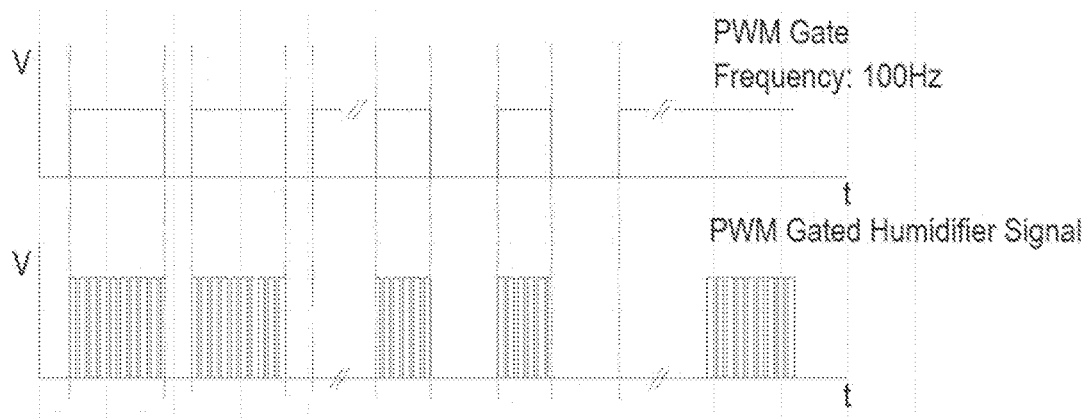

FIG. 5L illustrates relationship between the output signal Gate-PWM input into the AND gate(s) and the Gated PWM output signal for the humidifier output by the AND gate(s) in accordance with one form of the present technology.

Figure 5M:
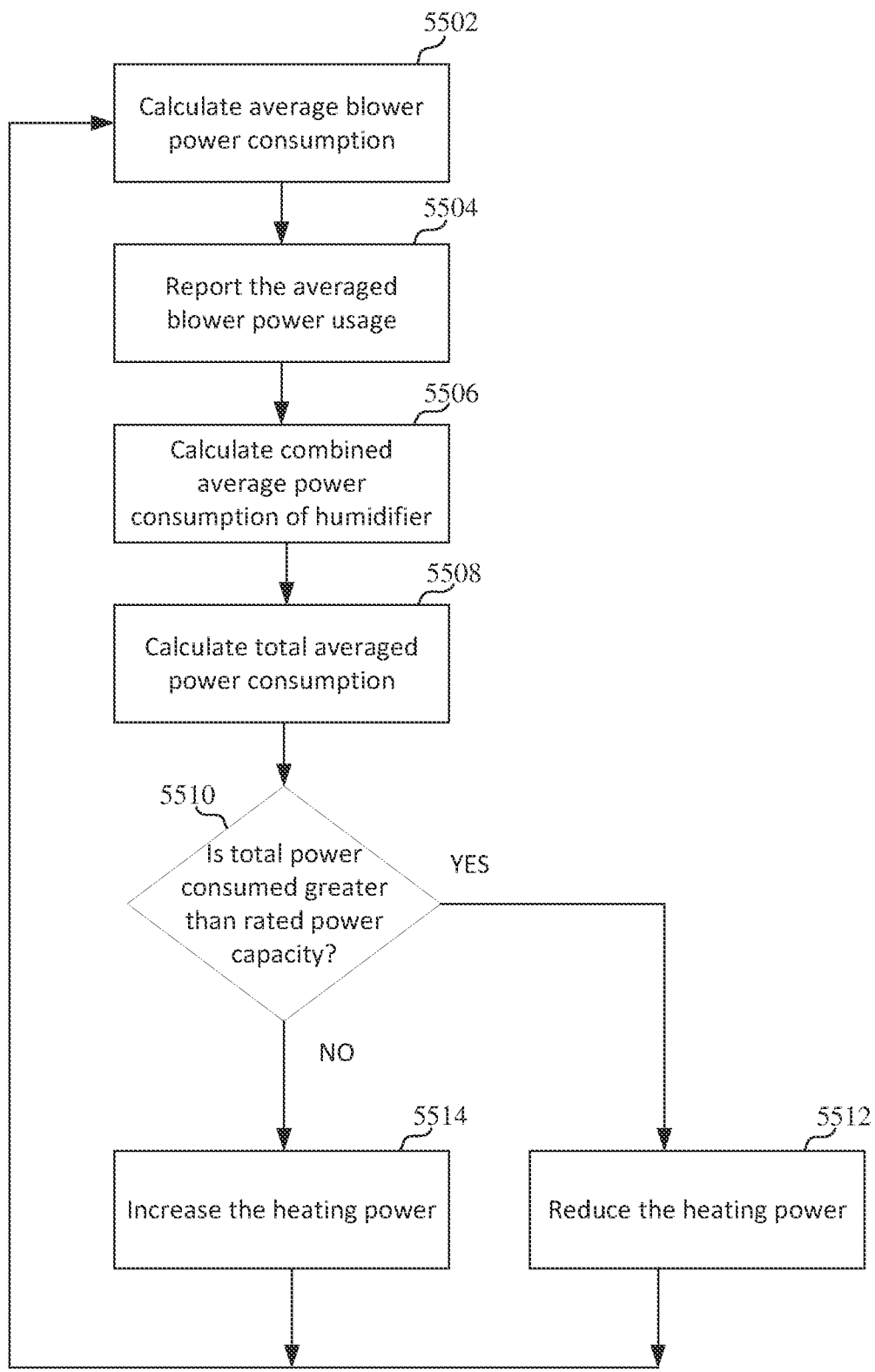

FIG. 5M shows a method for executing adaptive power management in one form of the present technology.

Figure 5N:
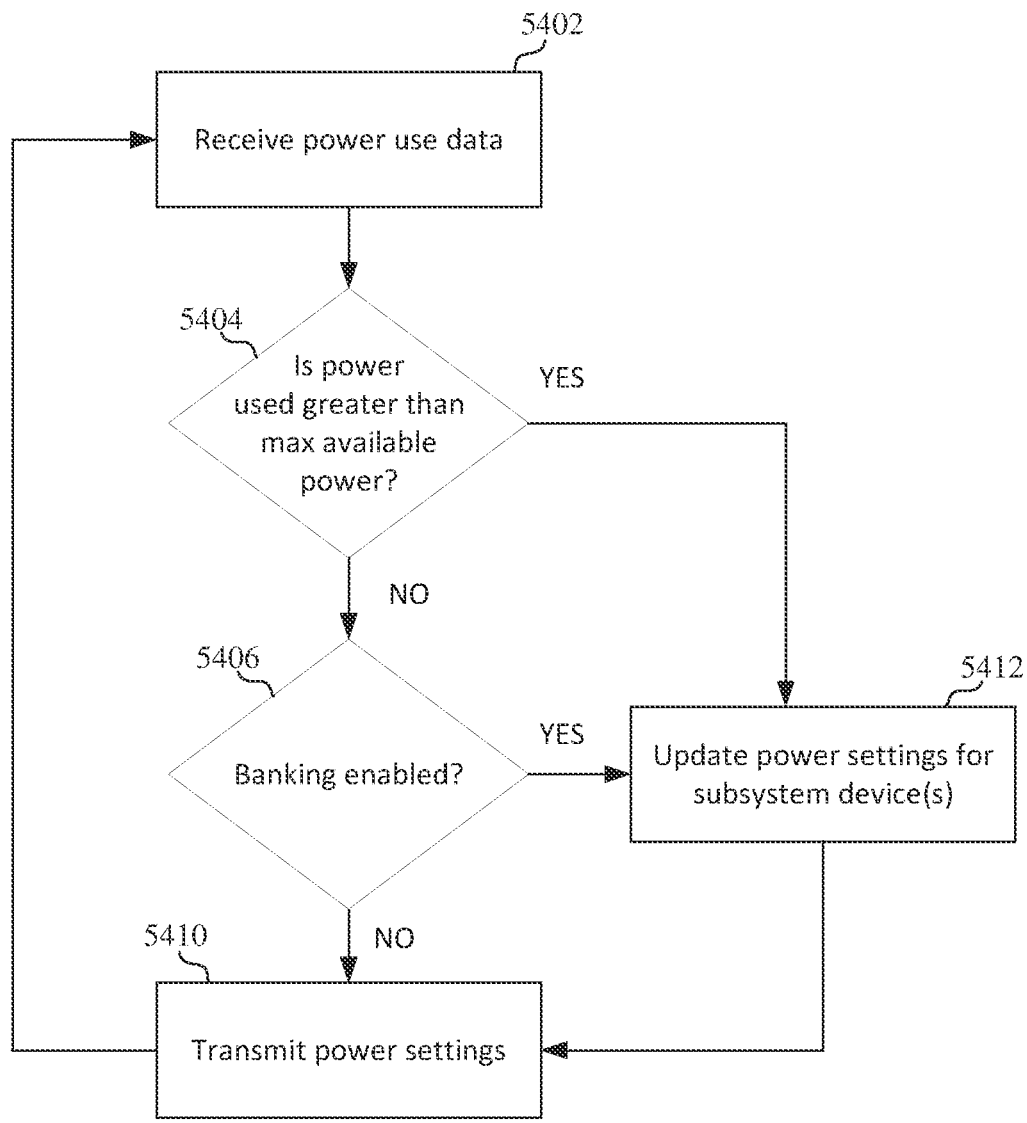
Figure 50:
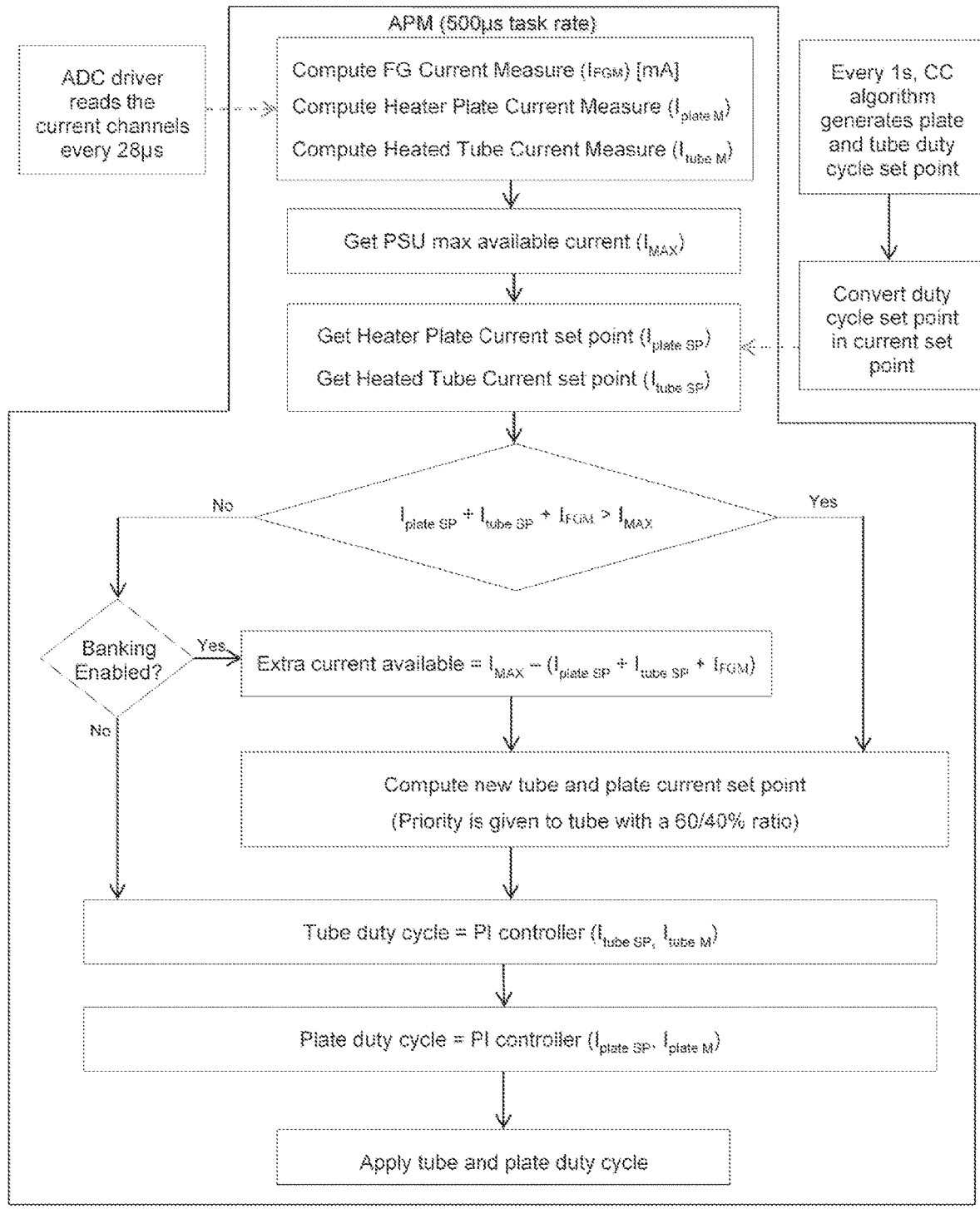

FIG. 5N shows a method for executing adaptive power management in another form of the present technology.

Figure 5P:
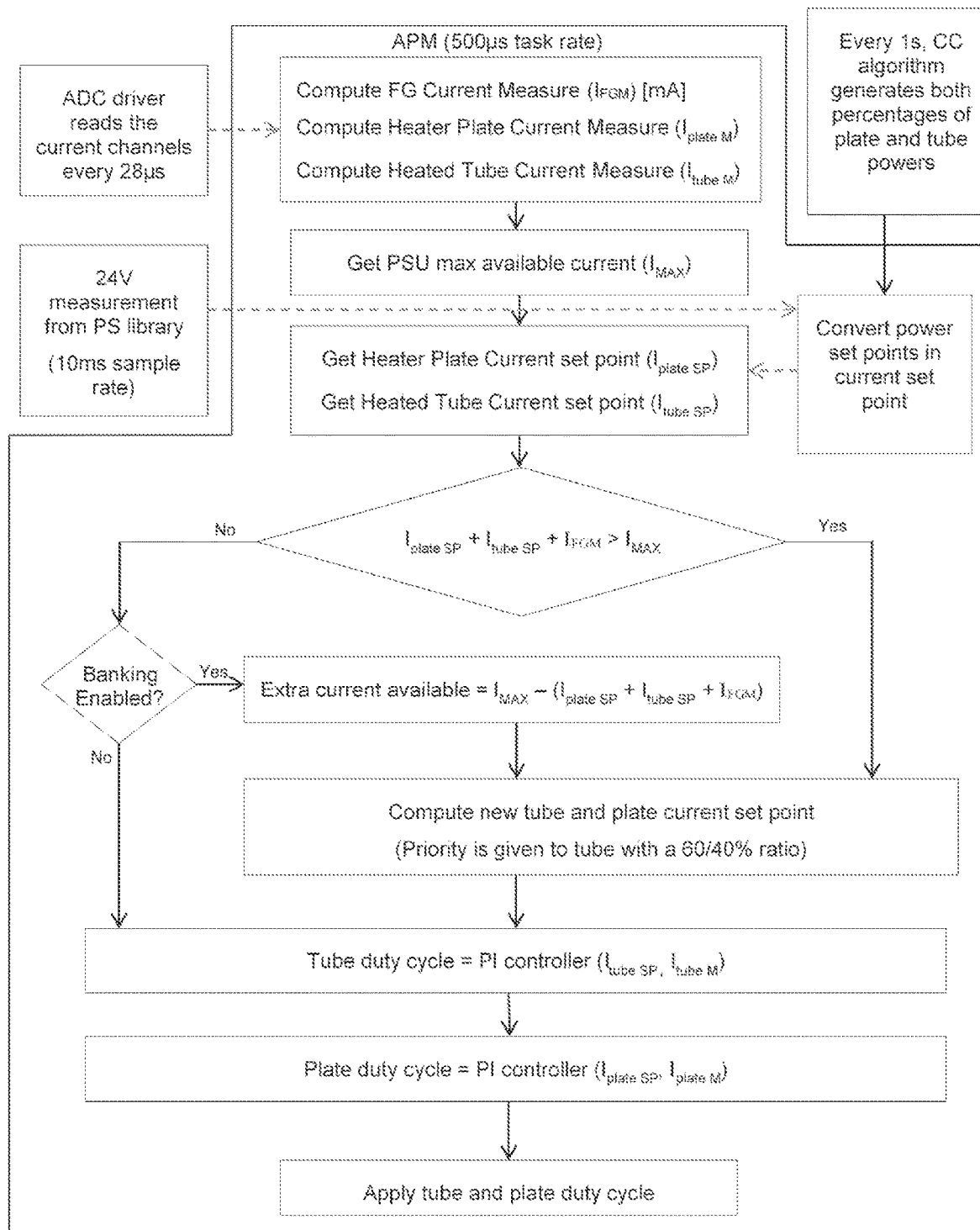

FIGS. 5O and 5P show more detailed methods for executing adaptive power management according to various forms of the present technology.

4.5 Breathing Waveforms

Figure 6A:
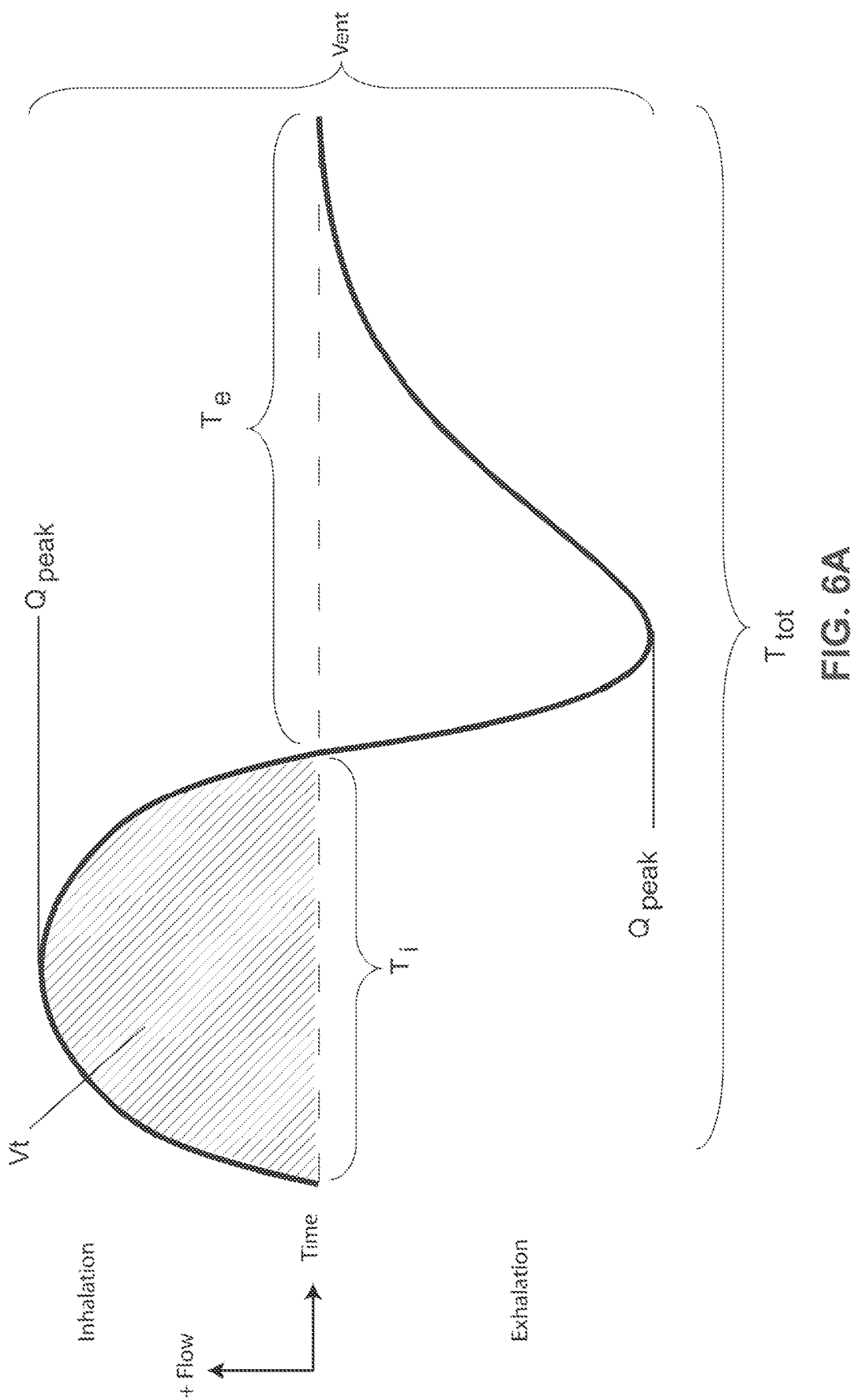

FIG. 6A shows a model typical breath waveform of a person while sleeping.

Figure 6B:
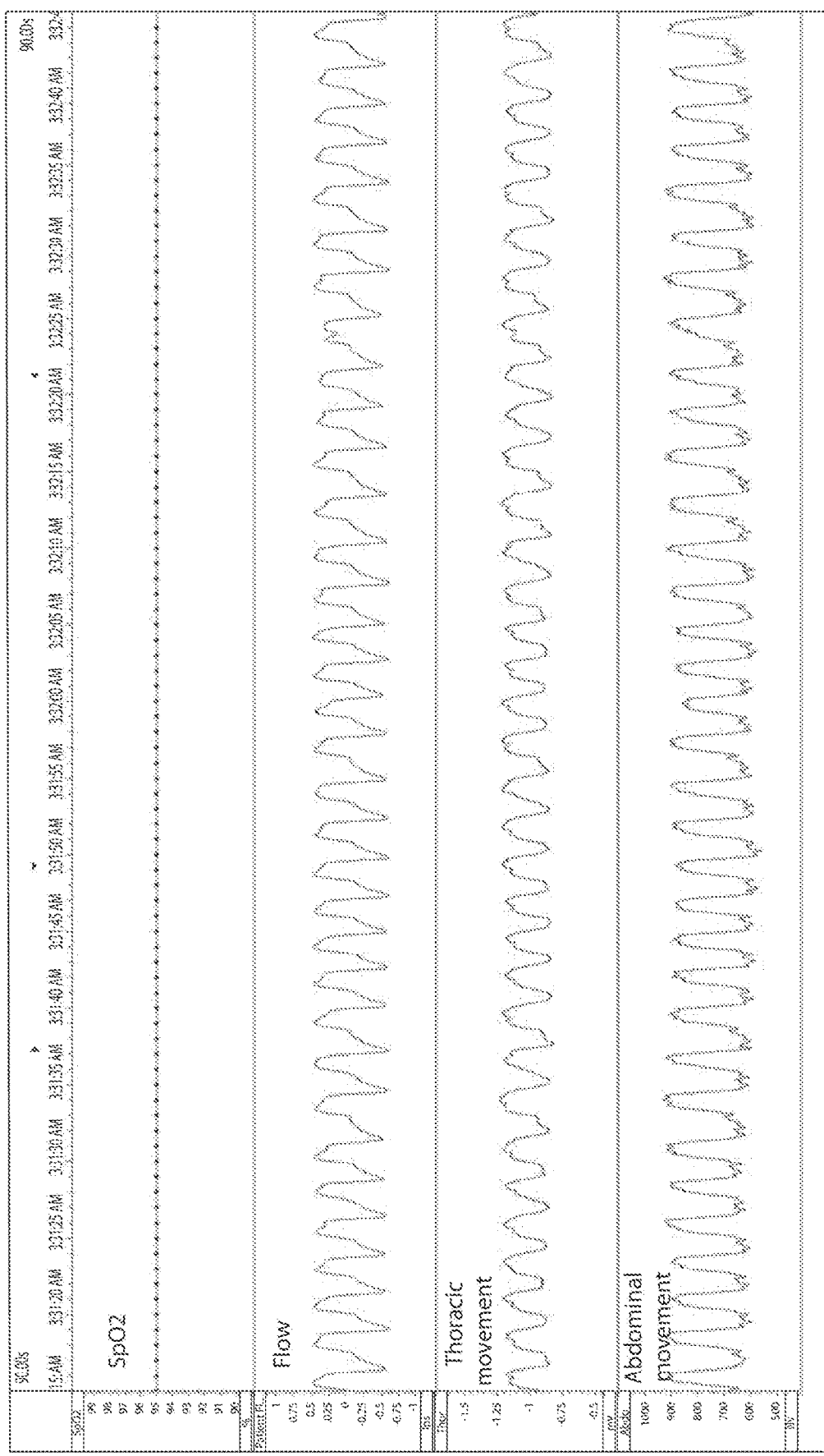

FIG. 6B shows selected polysomnography channels (pulse oximetry, flow rate, thoracic movement, and abdominal movement) of a patient during non-REM sleep breathing normally over a period of about ninety seconds.

Figure 6C:
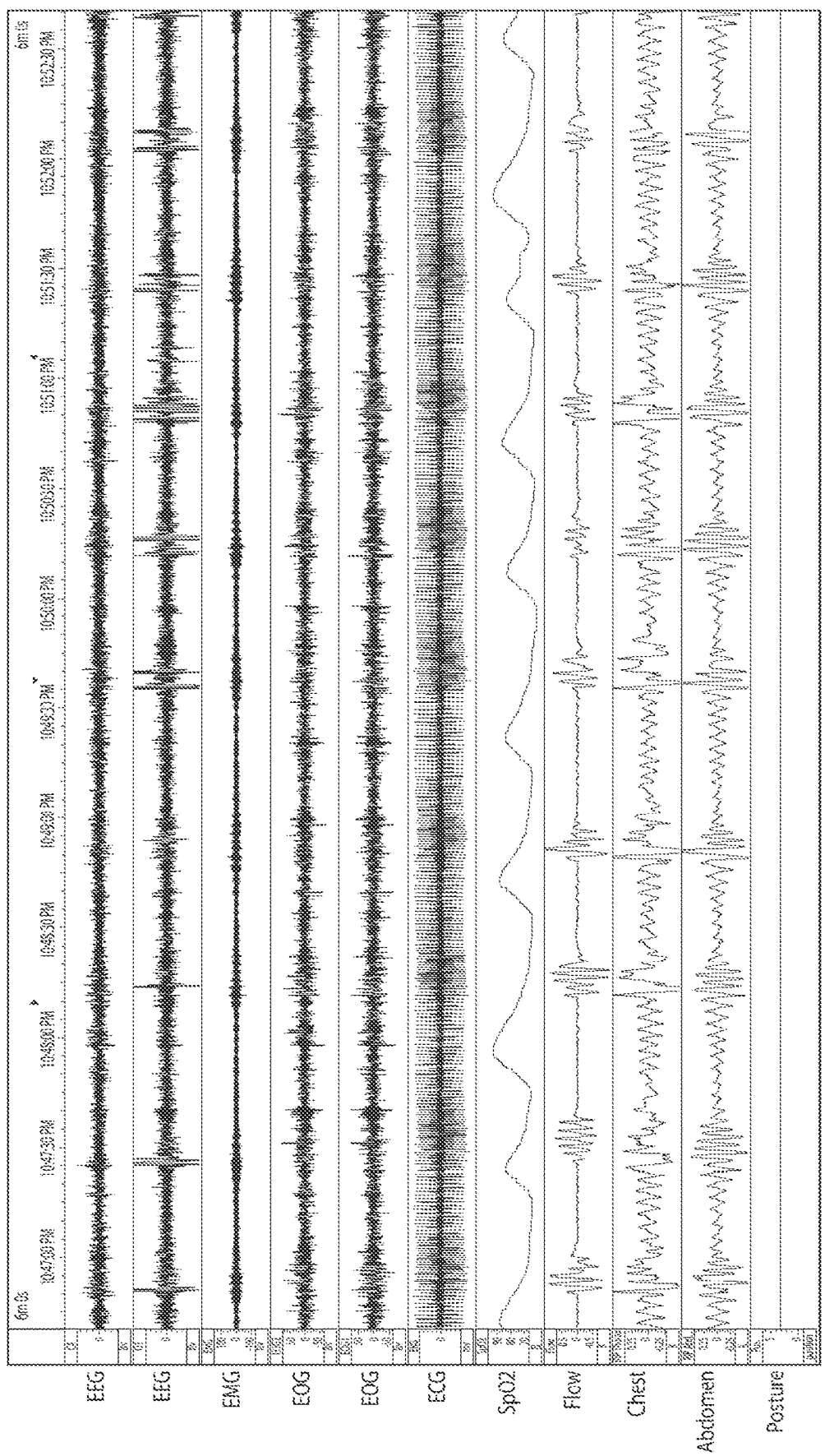

FIG. 6C shows polysomnography of a patient before treatment.

Figure 6D:
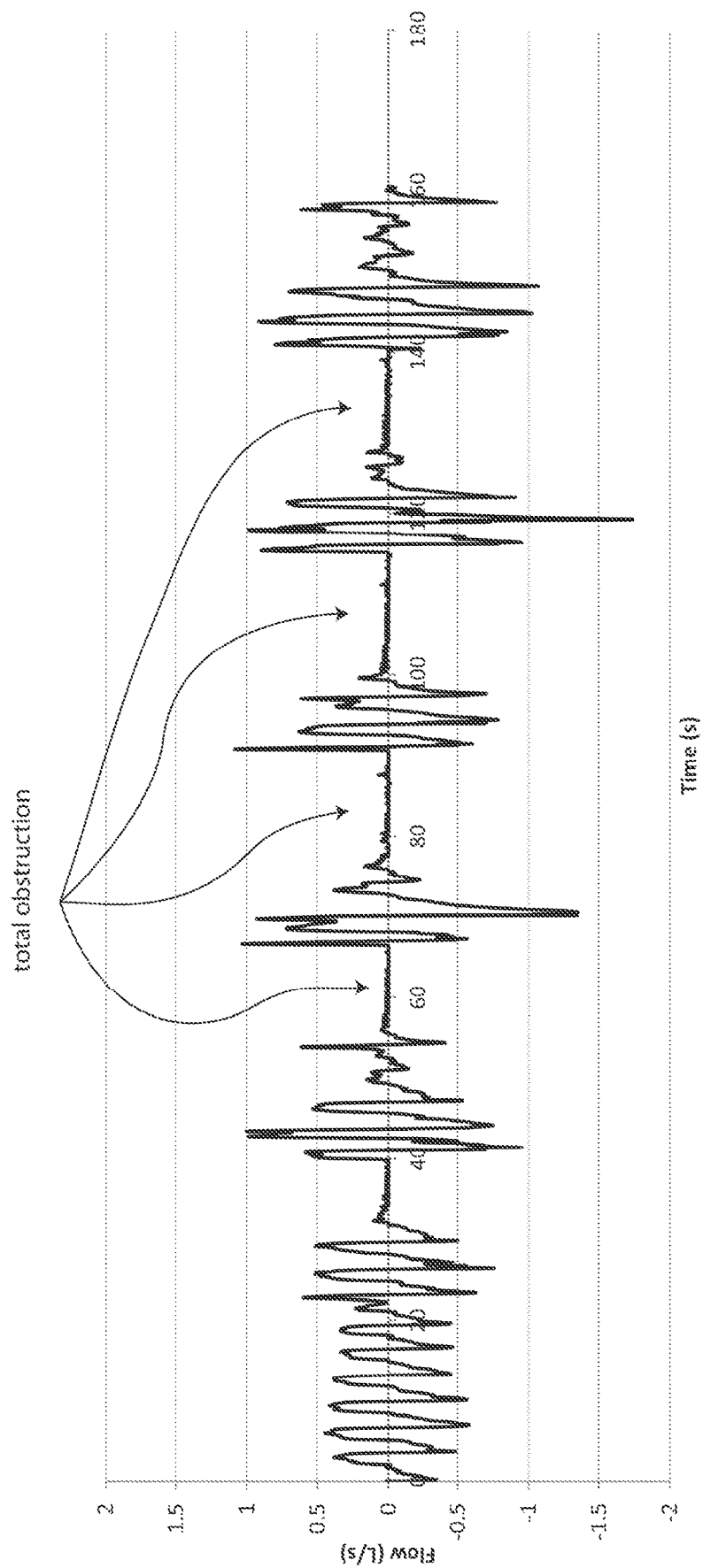

FIG. 6D shows patient flow rate data where the patient is experiencing a series of total obstructive apneas.

Figure 6E:
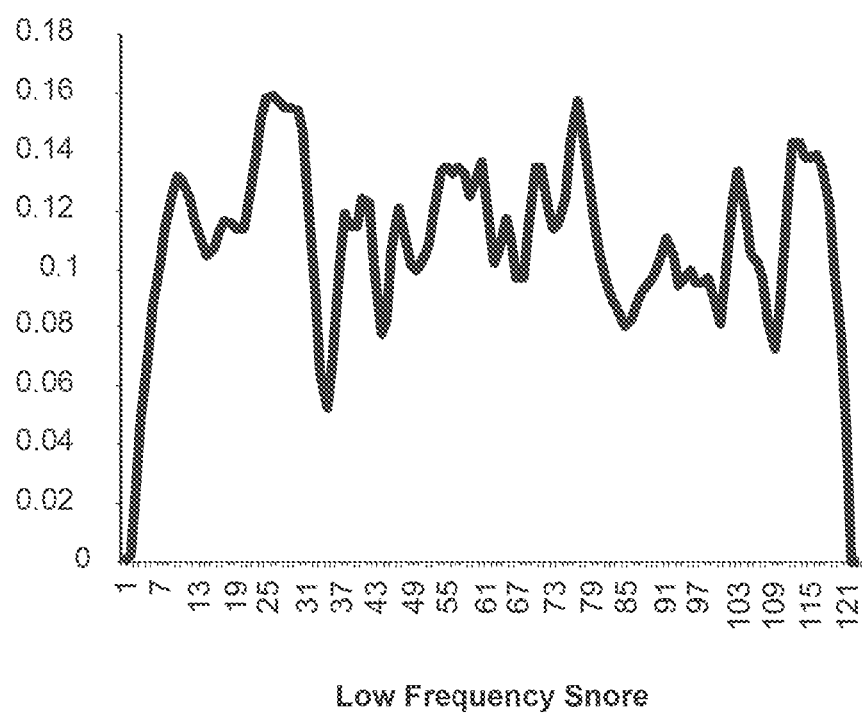

FIG. 6E shows a scaled inspiratory portion of a breath where the patient is experiencing low frequency inspiratory snore.

Figure 6F:
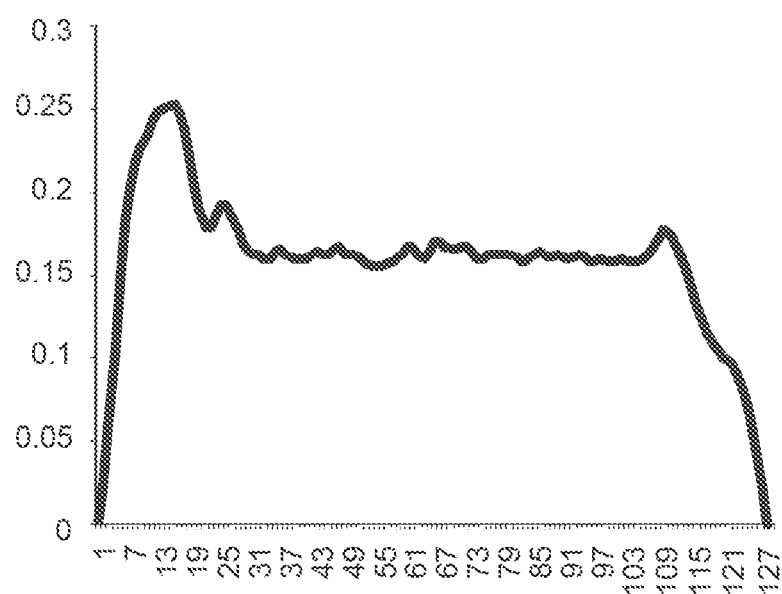

FIG. 6F shows a scaled inspiratory portion of a breath where the patient is experiencing an example of flattened inspiratory flow limitation.

Figure 6G:
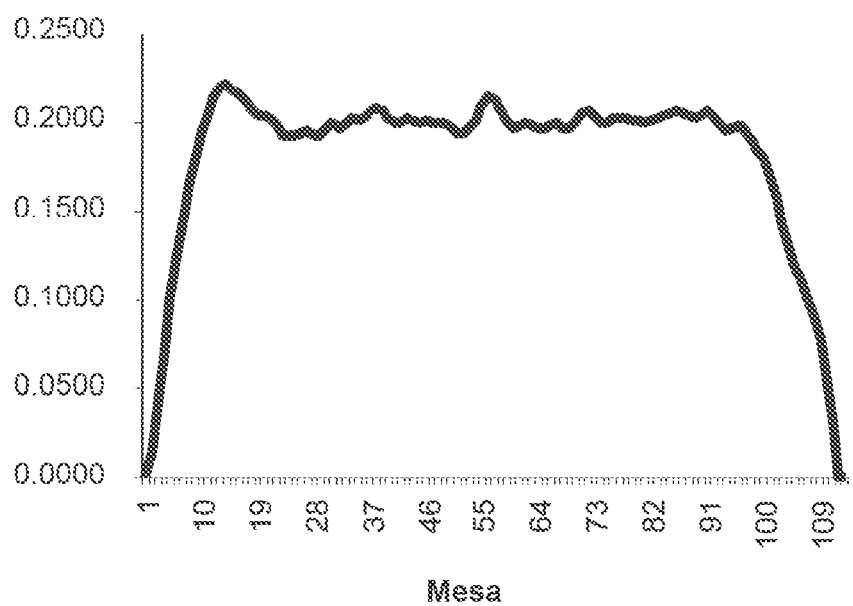

FIG. 6G shows a scaled inspiratory portion of a breath where the patient is experiencing an example of "mesa" flattened inspiratory flow limitation.

Figure 6H:
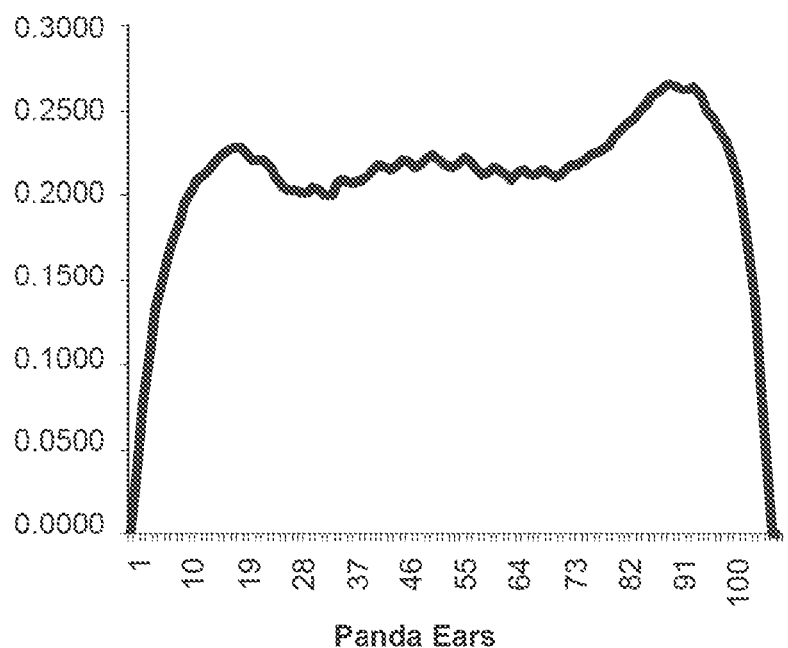

FIG. 6H shows a scaled inspiratory portion of a breath where the patient is experiencing an example of "panda ears" inspiratory flow limitation.

Figure 6I:

FIG. 6I shows a scaled inspiratory portion of a breath where the patient is experiencing an example of "chair" inspiratory flow limitation.

Figure 6J:
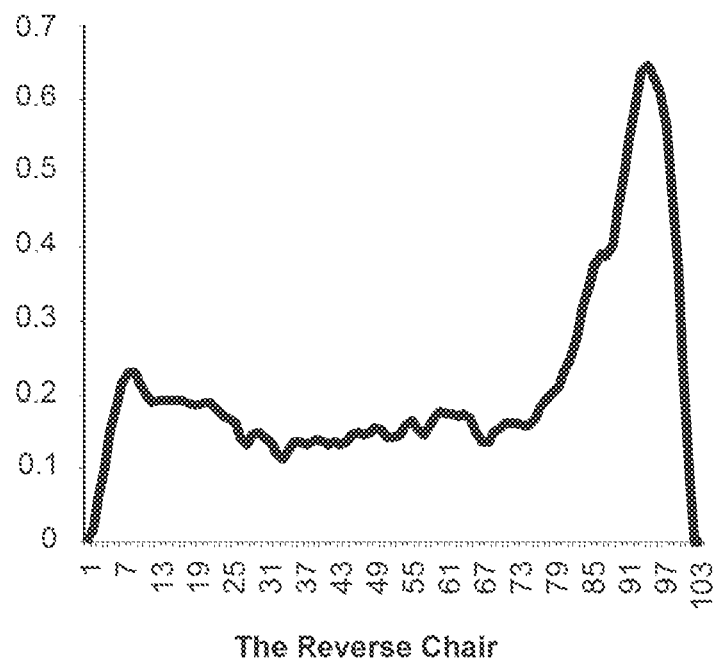

FIG. 6J shows a scaled inspiratory portion of a breath where the patient is experiencing an example of "reverse chair" inspiratory flow limitation.

Figure 6K:
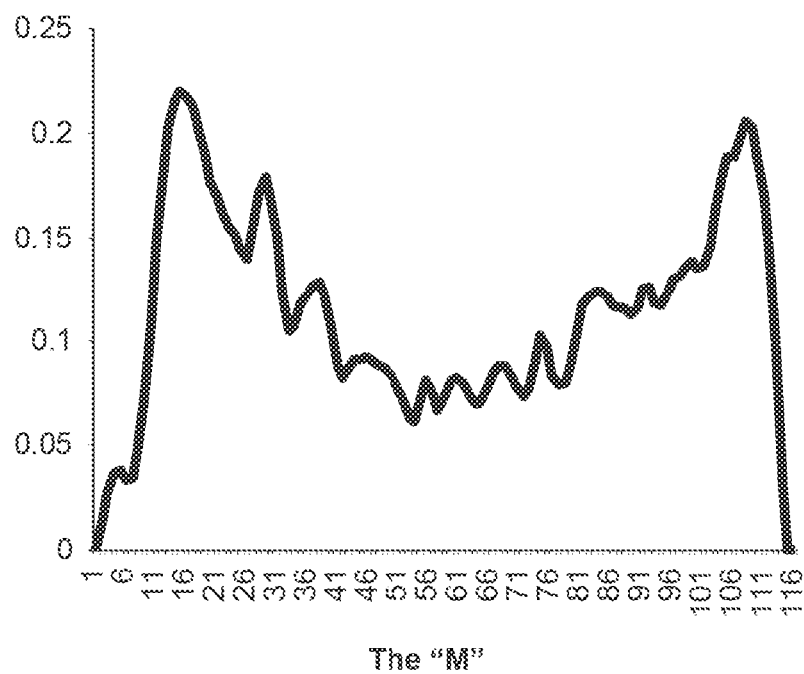

FIG. 6K shows a scaled inspiratory portion of a breath where the patient is experiencing an example of "M-shaped" inspiratory flow limitation.

Figure 6L:
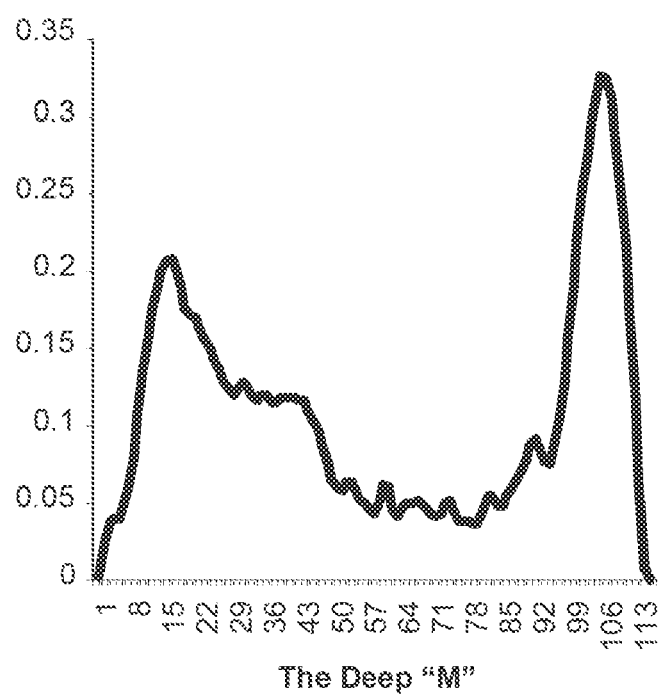

FIG. 6L shows a scaled inspiratory portion of a breath where the patient is experiencing an example of severely "M-shaped" inspiratory flow limitation.

Figure 6M:
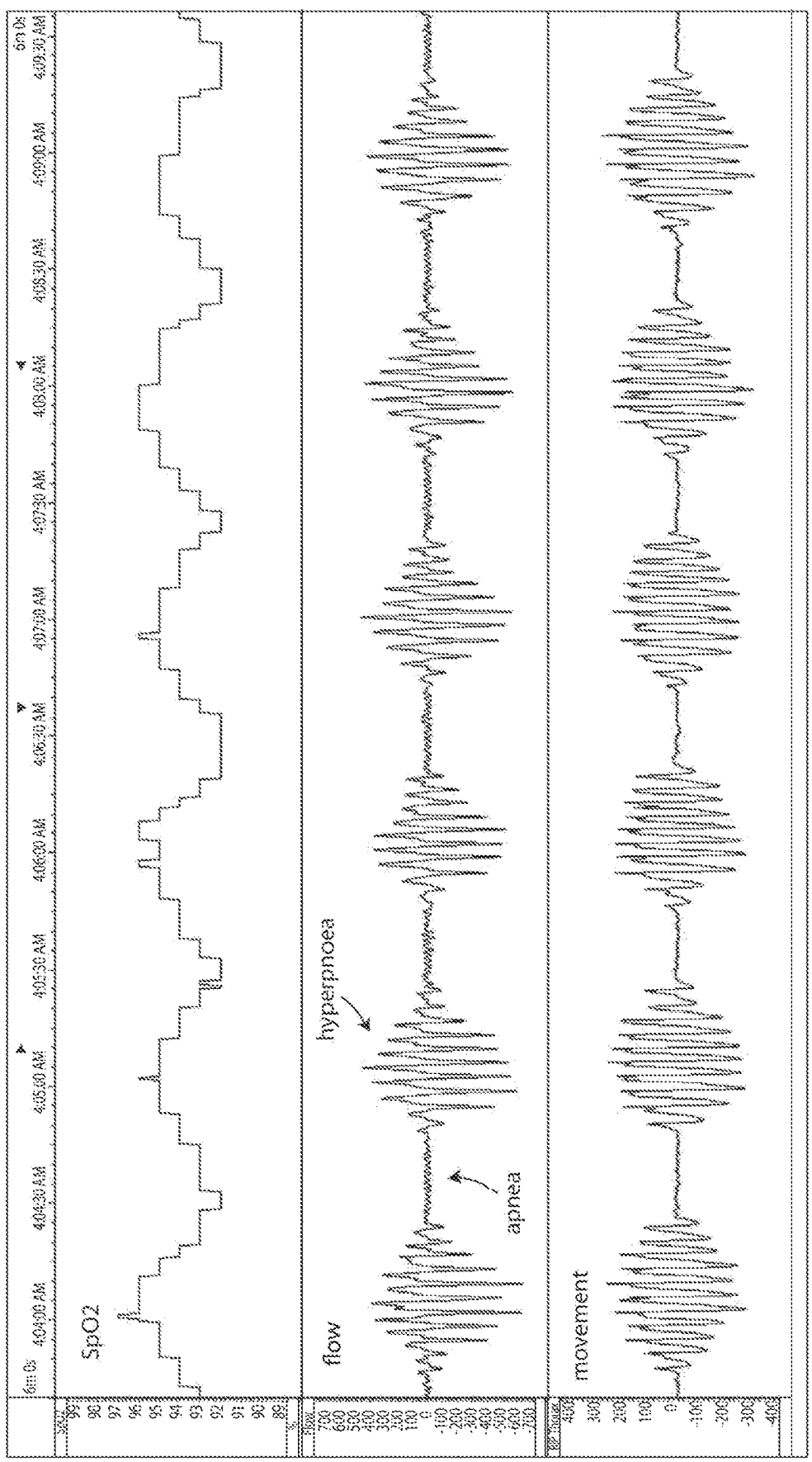

FIG. 6M shows patient data from a patient with Cheyne-Stokes respiration.

Figure 6N:
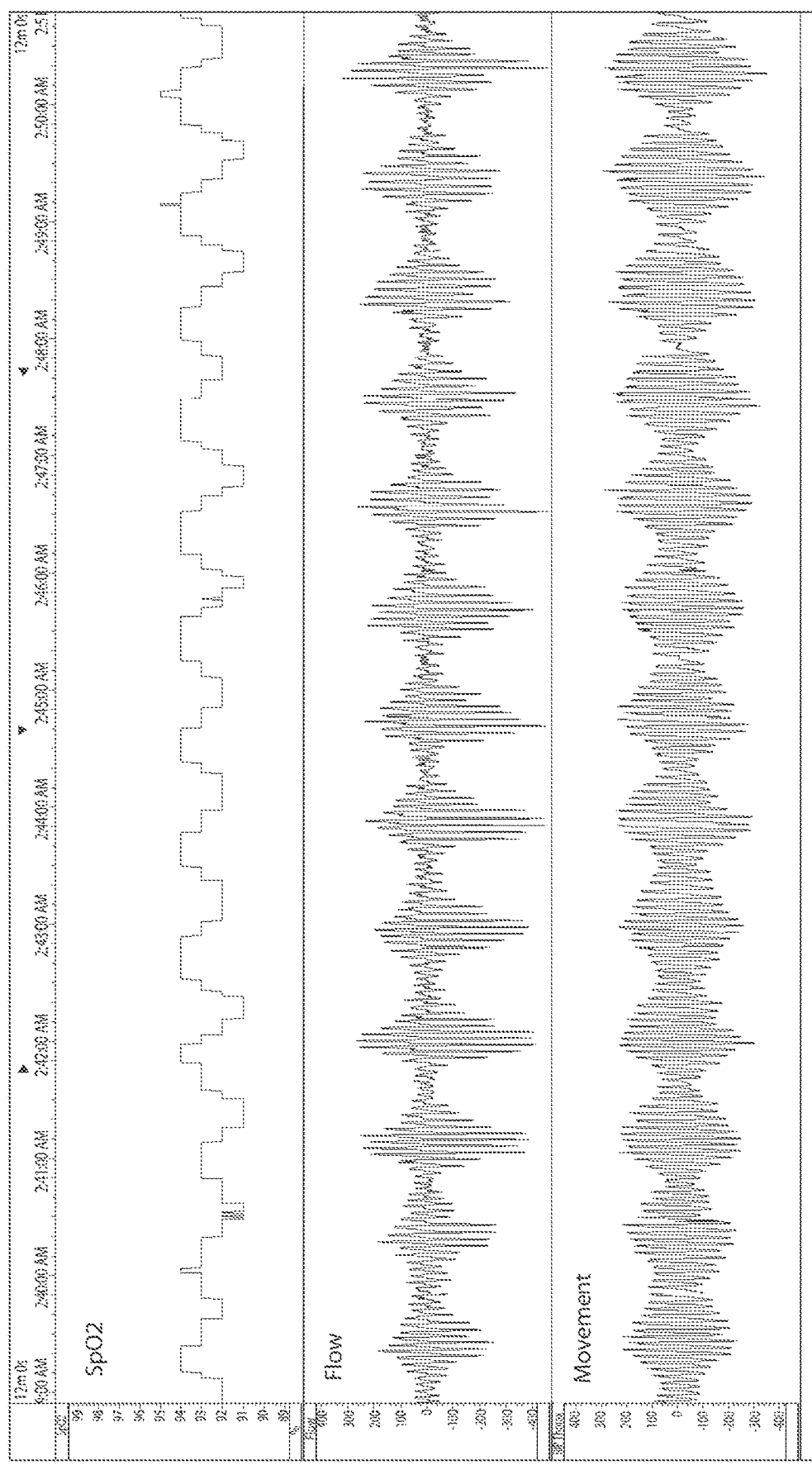

FIG. 6N shows patient data from a patient with another example of Cheyne-Stokes respiration, using the same three channels as in FIG. 6M.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and subsystem devices coupled directly or indirectly to the RPT device 4000. The subsystem devices may include humidifier 5000 and/or a heated tube. In some implementations of the present technology, the subsystem devices may be part of the RPT device 4000.

The power supply 4210 may receive power from an external power source (e.g., an A/C or DC power source) and/or include a battery to store electricity. The DC source may include an automobile battery, automobile outlet, fuel cell, and/or a solar panel. The power supply 4210 may be configured to charge the batteries when an external power source is available.

The power supply 4210 may be configured to provide 30, 60 and/or 90 watts of power. The power supply 4210 may include a converter configured to receive power in one form (e.g., from an A/C power source) and convert it to another form (DC power) used by the RPT device and/or one or more of the subsystem devices. In some implementations of the present technology, the power supply 4210 may include a DC converter (internal or external of the external housing 4010) to provide power to the system or to charge the batteries.

The power supply 4210 may include a main power supply and a secondary power supply. The main power supply may be coupled to an A/C power source (e.g., 240 volts at 50 Hz A/C or 120 volts at 60 hz A/C) and/or one or more batteries. The one or more batteries may power the RPT device 4000 in the absence of an A/C power source and/or when additional power is needed by the components of the RPT device 4000 and/or subsystem devices.

The power supply 4210 may not have sufficient power to simultaneously power the RPT device 4000 and subsystem devices. For example, the power supply 4210 may not have sufficient power to simultaneously power the blower 4142, a heater (e.g., a heater plate) in the humidifier 5000 and a heated tube. As will be discussed in more detail below, the RPT device 400 may include active power management to distribute power from power supply 4210 to the blower 4142 and one or more subsystem devices without triggering over current protection of the power supply 4210.

The power supply 4210 may include a current-limiting circuit configured to limit the output power when the output current exceeds the power supplies maximum rating by a predefined percentage (e.g., 110%, 120% or 150%) of power supply rating.

In one example, the power supply 4210 may be 24V/65 W rated—with 120% Over Current Protection (OCP) trigger (100 ms delay), and 150% OCP trigger (no delay). The heater plate may draw approximately 67.8 W (8.5Ω±5% @25° C.), the heated tube may draw approximately 57.7 W (9.3-10.9Ω@20-30° C.), and the blower may draw 40 W, which is limited by the pressure system software. As can be seen from this example, the total current consumption of all these components is much higher than the power the power supply 4210 is able to deliver. The active power management system is configured to manage the distribution of the power available without tripping the overprotection of the power supply. As will be discussed in more detail below, the power management may be entirely performed by software in some implementations of the present technology.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms pressure compensation 4312, vent flow rate estimation 4314, leak flow rate estimation 4316, and respiratory flow rate estimation 4318.

5.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.3.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase $\Phi$ of a current breathing cycle of a patient 1000.

In some forms, known as discrete phase determination, the phase output $\Phi$ is a discrete variable. One implementation of discrete phase determination provides a bi-valued phase output $\Phi$ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output $\Phi$ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase $\Phi$ equal to 0 (indicating inspiration) and 0.5 (indicating expiration) respectively.

Another implementation of discrete phase determination provides a tri-valued phase output $\Phi$ with a value of one of inhalation, mid-inspiratory pause, and exhalation.

In other forms, known as continuous phase determination, the phase output $\Phi$ is a continuous variable, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, a continuous value of phase $\Phi$ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.

4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase $\Phi$ is first discretely estimated from the respiratory flow rate Qr as described above, as are the inhalation time Ti and the exhalation time Te. The continuous phase $\Phi$ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase $\Phi$ of a respiratory cycle of a patient according to a waveform template $\Pi(\Phi)$.

In one form of the present technology, a waveform determination algorithm 4322 provides a waveform template $\Pi(\Phi)$ with values in the range [0, 1] on the domain of phase values $\Phi$ provided by the phase determination algorithm 4321 to be used by the therapy parameter determination algorithm 4329.

In one form, suitable for either discrete or continuously-valued phase, the waveform template $\Pi(\Phi)$ is a square-wave template, having a value of 1 for values of phase up to and including 0.5 revolutions, and a value of 0 for values of phase above 0.5 revolutions. In one form, suitable for continuously-valued phase, the waveform template $\Pi(\Phi)$ comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template $\Pi(\Phi)$ is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template $\Pi(\Phi)$ from a library of waveform templates, dependent on a setting of the RPT device. Each waveform template $\Pi(\Phi)$ in the library may be provided as a lookup table of values $\Pi$ against phase values $\Phi$. In other forms, the waveform determination algorithm 4322 computes a waveform template $\Pi(\Phi)$ "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation ($\Phi=0$ revolutions) or exhalation ($\Phi=0.5$ revolutions), the waveform determination algorithm 4322 computes a waveform template $\Pi$ "on the fly" as a function of both discrete phase $\Phi$ and time t measured since the most recent trigger instant. In one such form, the waveform determination algorithm 4322 computes the waveform template $\Pi(\Phi, t)$ in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template $\Pi(\Phi, t)$. In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \quad (1)$$

where:
A is the amplitude,
$\Pi(\Phi, t)$ is the waveform template value (in the range 0 to 1) at the current value $\Phi$ of phase and t of time, and
$P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:
Power failure (no power, or insufficient power)
Transducer fault detection
Failure to detect the presence of a component
Operating parameters outside recommended ranges (e.g. pressure, flow rate, temperature, $PaO_2$)
Failure of a test alarm to generate a detectable alarm signal.

Upon detection of the fault condition, the corresponding algorithm 4340 signals the presence of the fault by one or more of the following:
Initiation of an audible, visual &/or kinetic (e.g. vibrating) alarm
Sending a message to an external device
Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor 4274 provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature central conof a heated air circuit 4171 and/or a heating element controller 5252 configured to control the temperature of a heating element 5240.

5.7 Active Power Management

As discussed above, the power supply 4210 may not have sufficient power to simultaneously power the RPT device 4000 and the subsystem devices. While a power supply 4210 having sufficient power may be included with the RPT device 4000, power supplies with higher power ratings are more costly, take up more space, and/or are heavier. It is desirable to minimise the cost, space, and/or weight in RPT device 4000, and especially in portable RPT devices 400.

As an example, RPT device 4000 may utilize a compact design which compels use of a compact power supply 4210 (e.g., an external power supply). The compact power supply 4210 may have a smaller power capacity rating as compared to conventional power supplies. The RPT device 4000 may adopt a specific power management measure to work with the compact power supply 2410 without performance being compromised. The RPT device 4000 may fully utilize the power supply 4210 by dynamically managing the power demands of the subsystems (e.g., blower, the humidifier and/or functional circuits) of the RPT device 4000.

Implementations of the present technology provide for active power management of a power supply that does not have sufficient power to simultaneously power the RPT device 4000 and one or more subsystem devices. The active power management may include software and/or hardware configured to control the operation of the RPT device 4000 and subsystem device(s) in a manner that avoids triggering over current protection (e.g., provided by the protection circuit 4250) of the power supply 4210 while still providing treatment of respiratory conditions that utilizes the RPT device 4000 and the subsystem devices. Hardware based implementations of the power management are reliable but have the added cost of the additional components. Software based implementations of the power management are cheaper to implement but increase the software complexity. In some examples, the software based implementation may need additional memory to store the instructions but can use existing processing system for executing the instructions without needing additional processing component(s). A hybrid of hardware and software implementations of the power management may reduce the overall software complexity, provide better control than pure software based method and are less costly than pure hardware solutions. Hardware implementation may also be much faster to act. Including hardware component may increase processing speeds. Hardware based implementations may be much faster than software based implementation.

FIG. 5D shows an exemplary architecture of devices using power supplied by the power supply 4210. As shown in FIG. 5D, the power supply may be rated to provide 65 W of power. A controller 4230 and other components included in the RPT device 4000 (e.g., output devices, input devices and/or sensors) may use a maximum specified amount (e.g., 5 W) during operation. A blower 4142 may use a maximum of 40 W during operation. A heater 5020 (e.g., a heater plate) in the humidifier 5000 may use approximately 67.8 W. A heated tube 4172 including one or more heating elements and forming at least a portion of the air circuit 4170 may use approximately 57.7 W during operation. The total power that could be consumed by the devices illustrated in FIG. 5D if operated simultaneously exceeds the power rating of the power supply 4210. The blower 4142, heater plate 5020, and heated tube 4172 may be controlled so use only a portion of the power (e.g., at lower settings) and/or operate only during certain portions of the breathing cycle.

The RPT device 4000 may include circuitry to measure currents in the components illustrated in FIG. 5D. The measured currents may include: $I_{SYSTEM}$ representing the current supplied by the power supply 4210, $I_{FG}$ representing the current drawn by the system excluding the heater plate 5020 and the heated tube 4172, $I_{PLATE}$ representing the current drawn by the heater plate 5020, and/or $I_{TUBE}$ representing the current drawn by the heated tube 4172. The active power management includes controlling the operation of the blower 4142, heater plate 5020, and/or heated tube 4172 based on one or more of these current measurements. In some implementations of the present technology, the current drawn by the blower 4142 may be separately measured and used to the control the operation of the blower and/or other devices.

During operation, the treatment therapy being executed and conditions sensed by one or more sensors are used to determine how the blower 4142 is controlled. The blower 4142 has priority to the power provided by the power supply 4210. When the blower does not need all of the power available by the power supply, the excess power may be used to control the subsystem devices (e.g., the heater plate 5020, and/or heated tube 4172). The power for the blower may change based on the respiratory cycle of a patient and the blower may not use all of the available power during an inspiratory rise of a respiratory cycle and during an expiratory portion of the respiratory cycle. In some situations, the power for the blower may suddenly change due to a patient adjusting a mask or removing a mask.

FIG. 5E shows an exemplary architecture for controlling operation of multiple devices using power supplied by power supply 4210. A central controller 4230 may control operation of the RPT device 4000 and one or more subsystem devices based user inputs, sensor data, power available and/or power rating of the power supply 4210, and/or operating characteristics of the RPT device 4000 and one or more subsystem devices (e.g., a blower, a heater plate, a heated tube or other components such as a communication module).

The central controller 4230 may perform the control based on received current measurements from one or more current sensing circuits. As shown in FIG. 5E, the central controller 4230 receives current measurements from one or more current sensing circuits 5302-5308. Current sensing circuit 5302 may be configured to measure the current provided by the power supply 4210. Current sensing circuit 5304 may be configured to measure the current drawn by the blower 4142 and other subsystem devices, such as controllers, sensors and/or input devices. In some example, the current sensing circuit 5304 may be configured to only measure the current drawn by the blower 4142. Current sensing circuit 5306 may be configured to measure the current drawn by the heater plate 5020 (e.g., a first heating element). Current sensing circuit 5308 may be configured to measure the current drawn by the heated tube 4172 (e.g., a second heating element). The central controller 4230 receives the current measurements and determines which devices (e.g., blower, heater plate, and/or heater tube) should be powered and how much power should be provided to each of these devices without tripping the over current protection of the power supply.

The current sensing circuits 5302-5308 allow for the currents in different portions of the system to be monitored in real time so that the devices may be effectively controlled without triggering the over current protection of the power supply in response to changes in operating conditions of the devices. The current sensing circuits 5302-5308 may provide for a more accurate evaluation of the power being used by the devices as compared to estimating the power consumption based on predicted breathing cycle.

One or more of the current sensing circuits may comprise an ADC driver configured to read the current channels at predetermined intervals (e.g., every 28 μs). The current sensing circuits may receive analog signals representing the current and convert the analog signal to a digital signal for use by the central controller 4230. Implementations of the present technology, may use various current sensing circuits known to a person of ordinary skill in the art to obtain the current at different locations of the system. In some implementations, a digital current sensing IC could be used. The digital current sensing IC may be configured to split out the serial peripheral interface data.

The central controller 4230 may control the operation of the blower 4142 based on the chosen respiratory pressure therapy mode. The blower is given priority to the power from the power supply 4210 over other devices (e.g., the heater plate 5020 and heated tube 4172). The central controller 4230 limits the heater plate 5020 and the heated tube 4172 currents in order to maintain the global power consumption within the power supply 4210 power range. In some implementations, the power range may be limited in order to avoid tripping the overprotection of the power supply. In some implementations, the power range may include the power before overprotection is triggered in a very short timescale and the controller may average it out. The currents of the heater plate and/or heated tube are controlled fast enough to avoid triggering the power supply over current protection in case of fast rate of change of the blower current (e.g., due to patient disconnection or sudden changes in patients breathing). The active power management loop is executed faster than the execution of the blower controller loop. In one implementation of the present technology, the active power management may be executed two times faster (e.g., 0.5 ms) than the blower current closed loop (e.g., 1 ms).

The central controller 4230 may control the blower 4142, the heater plate 5020, and the heated tube 4172 via the blower controller 5310, the heater plate controller 5312, and the heated tube controller 5314, respectively. The central controller 4230 may determine current settings for the devices and send the set currents to the respective controllers. One or more of the controllers 5310-5314 may include a feedback control circuit configured to receive a current set for the respective device from the central controller 4230 and adjust the operation of the device until the measured current matches the current set for the device. In one implementation of the present technology, the controller for a specific device may modify a duty cycle of a pulse width modulated control signal provided to the device until the measured current matches the current set for the device.

In some implementations, one or more of the controllers 5310-5314 may be implemented with a proportional (P), proportional-differential (PD), proportional-integral (PI), or proportional-integral-differential controller (PID). These controllers may compute and transmit an updated control output signal every sample time to the device is controlled. The settings determined by the active power management for the PI controller(s) may be determined based on the measured currents faster than (e.g., two times faster) than the PI controller of the blower 4142. The controllers 5310-5314 may be embedded in a central processor (e.g., a microprocessor).

Determining the settings for the one or more of the controllers 5310-5314 may include determining a set point (e.g., duty cycle) for the devices using a climate control algorithm and adjusting the set point based on one or more measured currents. In one example, the duty cycle set points for the heater plate 5020 and the heated tube 4172 may be determined using a climate control algorithm and then adjusted based on the measured current draw of the blower 4142. The duty cycle set points for the heater plate 5020 and heated tube 4172 may be decreased to avoid triggering the power supply over current protection or increased to use extra available power to provide additional heat by the heater plate 5020 and/or the heated tube 4172.

The additional heat generated when power is available may compensate for the lack of heat provided during periods of time when additional power is needed by the blower and power is limited to the heater plate 5020 and the heated tube 4172.

In some implementations, a respective controller 5310-5314 may include a respectively coupled current sensing circuit 5304-5308 or receive measurements of the current from the respectively coupled current sensing circuit 5304-5308. The controllers 5310-5314 may use the measured currents and the set currents to control the operation (e.g., a duty cycle of a pulse width modulated control signal) of the respective device.

In some implementations of the present technology, the heater plate controller 5312 may receive a budgeted current for the heater plate 5020 and, based on the budgeted current and the measured current by the sensing circuit 5306, adjust the pulse width modulated control signal such that all of the budgeted current for the heater plate is used by the heater plate 5020. The heated tube controller 5314 may receive a budgeted current for the heated tube 4172 and, based on the budgeted current and the measured current by the sensing circuit 5308, adjust the pulse width modulated control signal such that all of the budgeted current for the heated tube is used by the heated tube 4172.

In some implementations of the present technology, the pulse width modulated signals for the blower, heater plate, and/or the heated tube may be offset from each other. In some examples, the pulse width modulated signal may be offset as a function of a detected patient respiratory cycle. Examples of offsetting peak power operation of the devices are disclosed in U.S. Pat. No. 8,844,522 "Power Management in Respiratory Treatment Apparatus".

Example of Dynamic Power Management

To meet the therapy requirement, the power need of the blower should be guaranteed at any time without being compromised. This forms the basis of the dynamic power management. The humidifier and the rest of the circuits could have temporary compromised power allocation. The humidifier can use as much power as it can absorb from the remaining power not used by the blower. If a power supply has 65 W capacity and the blower is drawing 5 W during therapy, the humidifier can be allowed to draw up to 60 W rather than limit itself to a predefined figure. Three power management concepts could be implemented in the RPT device 4000 using hardware method, software method, or combined software and hardware method.

The power management may be performed based on measurements of power consumed by components of the RPT device 4000. FIGS. 5F and 5G illustrate exemplary power measurement of components in the RPT device 4000. The RPT device 4000 may include current sensing and amplification circuits for the blower 4142, the heater plate 5020, and/or the heated tube 4172. The waveforms may be measured at the output of the amplifiers during operation of the RPT device 4000. During operation of the RPT device 4000, operation the heater plate 5020, and/or the heated tube 4172 may be controlled to operation at their maximum level.

Waveform 6010 represents total current drawn by RPT device 4000 (e.g., on a 24V line). Waveform 6020 represents blower 4142 current sensing voltage (e.g., with reversed polarity). Waveform 6030 represents the heater plate 5020 current sensing voltage. Waveform 6040 represents the heated tube 4172 current sensing voltage.

FIG. 5G shows a portion of the waveforms shown in FIG. 5F enlarged. As shown in FIG. 5G, the heated tube 4172 and heater plate 5020 share the power use, which means that the heating elements for the humidifier plate and the heat tube are turned on alternatively. When the humidifier PWM (represented by waveform 6030) is on, the heat tube PWM (represented by waveform 6040) is off. Similarly, when the heat tube PWM (represented by waveform 6040) is on, the humidifier PWM (represented by waveform 6030) is off. In some examples, the PWM signals for the heater plate 5020 and the heated tube 4172 will not be on at same time, but they can both be turned off at any time. In some example, one of the PWM signals for the heater plate 5020 or the heated tube 4172 may be turned on while the other may remain off for a plurality of cycles. As shown in FIG. 5G, for a portion of time the PWM signals for the heater plate 5020 and the heated tube 4172 may be turned off to ensure that both PWM signals to not draw power at the same time.

FIG. 5H shows example circuitry that may be used for measuring power used by the RPT device 4000. While specific circuit components are illustrated in FIG. 5H, they are not so limited and may be substituted by one or more other components providing similar functionality.

The circuitry includes sensing, summing, and filtering circuitry. The sensing circuitry may be configured to measure the current drawn by the blower 4142 and subsystem devices (e.g., a heated tube 4172 and/or a heater plate 5020). The summing circuitry may be configured to output a voltage that is proportional to the current drawn by the blower 4142 and the subsystem devices (e.g., a heated tube 4172 and/or a heater plate 5020). The filtering circuitry may be configured to filter out high frequency signals to provide an averaged total power consumption.

In FIG. 5H, the blower current sensing signal may be buffered and amplified by Op-amp 6050. The output of the Op-amp 6050 is coupled to Op-amp 6052 via a resistor. While not shown in FIG. 5H, current sensing signals from one or more subsystem devices (e.g., the plate and tube) may also be buffered and amplified. Op-amp 6052 may receive voltages representing the blower current and the heating currents (including the humidifier and the heat tube) and provide an output representing the summed voltages. By carefully choosing the input resistors, the output voltage of the Op-amp 6052 will be proportional to the total power consumption. The voltage then may be passed through a low pass filter (LPF) including Op-amp 6054, and capacitor 6066 and resistor 6068. The output V_ctrl of LPF represents the averaged total power consumption (Power-I-F). The polarity of V_ctrl may be reversed, which means that the higher V_ctrl, the lower the total power consumption it represents. In an alternative form of the present technology, the polarity of V_ctrl may not be reversed, which means that the lower the V_ctrl, the more power is available for consumption.

FIG. 5I shows exemplary signal waveforms for circuitry shown in FIG. 5H. The waveforms Motor-I, Plate-I and Tube-I show voltage values over time representing the current drawn by the RPT device 4000. The blower may draw higher current during patient inhalation and less current during expiration. The heating of the heat plate and the heat tube are PWM signal controlled. As discussed above, in one form of the present technology, the heating PWM signals for the plate and tube are controlled so that at any time there is only one heating element on.

Sum-I represents the sum the voltages representing the blower current and the heating currents (including the humidifier and the heat tube) and is proportional to the total power consumption. Filtered power average represents a low-pass filtered Sum-I signal. The Filtered power average may be used as a control signal V_ctrl for controlling the operation of the heating elements.

FIG. 5J shows power control circuitry that may be used for controlling operation of the heating elements based on a control signal representing power consumption of the RPT device 4000 in accordance with one form of the present technology. While specific circuit components are illustrated in FIG. 5J, they are not so limited and may be substituted by one or more other components providing similar functionality.

The power control circuitry is configured to receive control signal V_ctrl and one or more PWM signals used for controlling operation of subsystem devices (e.g., a heated tube 4172 and/or a heater plate 5020). In one form of the present technology, the control signal V_ctrl may be provided by the circuitry illustrated in FIG. 5H. The power control circuit may be configured to modify the one or more of the PWM signals based on the control signal V_ctrl.

In one form of the present technology, the one or more of the PWM signals are modified when the control signal V_ctrl reaches a predetermined threshold representing a control limit. When the total power (represented by V_ctrl) is below a control limit, the power control circuit may provide the PWM signals to the subsystem devices without modification of the received PWM signals. When the total power (represented by V_ctrl) reaches or exceeds the control limit, the power control circuit may modify the one or more PWM signals.

In FIG. 5J, a voltage controlled PWM circuit 6070 receives control signal V_ctrl and outputs a Gate PWM signal for controlling the heat plate input signal (Heat-Plate—PWM—In) and/or the heat tube input signal (Heat-Tube—PWM—In). The duty cycle of the output signal (Gate-PWM) is controlled by the control signal V_ctrl. In some examples, the output (Gate-PWM) may be provided at a present frequency (e.g., 100 Hz). One or more resistors, capacitors, and/or voltage sources (e.g., VCC) may be used to control the operation parameters of the voltage controlled PWM circuit 6070.

In one example, the voltage controlled PWM circuit 607 may be configured to increase the duty cycle of the output signal Gate PWM when the control signal V_ctrl is high (low power consumption) and reduce the duty cycle of the output signal Gate PWM when the control signal V_ctrl is low (high power consumption). An AND gate 6072 may receive the output signal Gate-PWM and the heat plate input signal (HeatPlate—PWM—In), and output a gated output signal (HeatPlate—PWM—Out) for the heating element in the heater plate 5020. An AND gate 6074 may receive the output signal Gate-PWM and the heat tube input signal (HeatTube—PWM—In), and output a gated output signal (HeatTube—PWM—Out) for the heating element in the heated tube 4172. The reduction or increase in the duty cycle of the output signal Gate PWM will generate a reduction or increase in the power provided to the heating elements.

The voltage controlled PWM circuit 6070 may be configured to include one or more thresholds for controlling how the control signal V_ctrl changed the duty cycle of the output signal Gate PWM. FIG. 5K illustrates output signal Gate-PWM duty cycle being proportional to the control signal V_ctrl in accordance with one form of the present technology. The waveform in FIG. 5K depicts the heating power control by using low frequency (100 Hz) gate PWM signal, the duty cycle of which is controlled by V_ctrl (reversely proportional to total power consumption).

A first threshold V1 may be set so that when control signal V_ctrl is higher than the threshold (less than the PSU's power rating), the output signal Gate PWM will be at 100% duty cycle, which means there is no power limitation to the heating circuit(s). When the control signal V_ctrl is lower than the threshold V1, the duty cycle of the output signal Gate PWM may be reduced so that the power used by the heating circuit(s) is reduced. FIG. 5K shows that the threshold is set so that when control signal V_ctrl is low (high power consumption), the output signal Gate PWM duty cycle is low and less heating PWM signal passes through the gate and hence less averaged heating power. When control signal V_ctrl is high (low power consumption), the output signal Gate PWM duty cycle is high and hence more averaged heating power.

A second threshold value V2 may be set so that when the control signal V_ctrl is between the first threshold value V1 and the second threshold value V2, the output signal Gate PWM duty cycle is set to a first value (less than 100%), and when the control signal V_ctrl is lower than the second threshold value V2 the output signal Gate PWM duty cycle is further reduced (e.g., a second value that is lower than the first value).

In one form of the present technology, when the control signal V_ctrl is between the first threshold value V1 and the second threshold value V2, the duty cycle may be reduced below 100% proportionally value of the control signal V_ctrl, and when the control signal V_ctrl is lower than the second threshold value V2 the output signal Gate PWM duty cycle is reduced further (e.g., to 0, so that no heating power is provided to the heating elements).

FIG. 5L illustrates relationship between the output signal Gate-PWM input into the AND gate(s) and the Gated PWM output signal for the humidifier output by the AND gate(s) in accordance with one form of the present technology. As shown in FIG. 5L, when the value of the PWM Gate signal is zero, the Gated PWM output signal for the humidifier is zero, reducing the power consumed by the heating element (s). When the value of the PWM Gate signal is not zero, the received PWM gated humidifier signal is provided to the heating element(s).

In one form of the present technology, dynamic power management may be implemented purely by software. FIG. 5M shows a method for executing adaptive power management in one form of the present technology. The dynamic power management method that may be performed by executing instructions stored in non-transitory memory. In one example, a central controller 4230 and/or a humidifier controller 5250 may be configured perform the operations shown in FIG. 5M. While the operations in FIG. 5M are discussed with reference to specific controllers (e.g., a central controller 4230 and/or a humidifier controller 5250) embodiments of this disclosure are not so limited, and may be performed by a single controller or additional controllers.

In step 5502, the central controller 4230 monitors the blower current is in real time and calculates an averaged blower power consumption. The averaged blower power consumption may be calculated at a predetermined frequency. In one example, the frequency may be 100 Hz. In other examples, the frequency may be higher or lower depending on the humidifier controller's workload. The frequency may be set lower as long as it does not cause the current overprotection of the power supply to trigger.

In step 5504, the central controller 4230 reports the averaged blower power usage to the humidifier controller 5250.

In step 5506, the humidifier controller 5250 calculates the combined average power consumption of the heater plate 5020 and/or the heated tube 4172. The combined average power consumption of the heater plate 5020 and/or the heated tube 4172 may be calculated at the same frequency as the central controller 4230 performing the calculation of the averaged blower power usage (e.g., 100 Hz).

In step 5508, the humidifier controller 5250 calculates the total averaged power consumption. The total averaged power consumption may include the estimated power consumption of other circuits in the RPT device and/or devices coupled to the RPT device.

In step 5510, the total averaged power consumption is compared to a rated power capacity of the power supply unit. If the total averaged power is over the power supply rated power capacity (e.g., 65 W) (YES in Step 5510), then the humidifier controller 5250 reduces the heating power to the humidifier circuit (Step 5512). If the total averaged power is under the power supply rated power capacity (NO in step 5510), then the humidifier controller 5250 may increase the heating power to the humidifier circuit. The heating power to the humidifier circuit may be increased if there is need for increased heat to be produced in the heater plate 5020 and/or the heated tube 4172. The heating power to the humidifier circuit may be increased as long as the total power is kept under the rated power capacity limit of the power supply.

In one form of the present technology, the implementation in software may need to have priority in processing the power calculation and controlling the RPT device 4000 based on: the central controller 4230 calculating the blower power consumption at predefined frequency, the central controller 4230 sending the blower power figure to the humidifier controller 5250, and the humidifier controller 5250 calculating the total power consumption and controlling the heating power output.

The software implementation may need to be fast in responding to the total power variations. If the software implementation is not fast enough, the power supply unit may temporarily overload and the power supply unit OCP may be triggered.

In one form of the present technology, hardware may be used to acquire the total power consumption (e.g., represented by V_ctrl) and software based processing may be used to limit the power consumption. The power consumption signal V_ctrl may be connected to an A/D input of the humidifier controller 5250 (e.g., microcontroller). With this implementation, the humidifier controller 5250 can get the total power consumption without consume too much of its calculation capacity.

In this example, the heating power control by the humidifier control may be similar to the operations discussed above with reference to FIG. 5M. The difference with the implementation using the central controller 4230, is that there is no need for the central controller 4230 to calculate the power usage and to send the blower power consumption figures to the humidifier controller 5250.

FIG. 5N shows a method for executing adaptive power management in another form of the present technology. In one form of the present technology, the method may be executed by software and/or hardware. The method may be executed by a processing system including one or more processors. In one form of the present technology, the method may be executed at least partially by a central controller 4230.

The method includes receiving power use data (step 5402). The power use data may include data representing the power available and/or being provided by the power supply and/or power used by the device, or by subsystems of the medical device. The power use data may include current supplied by the power supply, current drawn by the medical device, and/or current drawn by one or more subsystem devices. In one form of the present technology, the power use data may include the current supplied by the power supply, current drawn by the medical device including a blower without the subsystem devices, current drawn by one or more components of a humidifier, and/or current drawn by one or more components of a heated tube.

The method includes determining whether the power used is greater than the maximum available power (step 5404). This determination may be made based on the rating of the power supply and/or remaining charge of the power supply, the received power use data, and/or power setting being applied to the one or more subsystem devices. In one form of the present technology, the determination of whether the power used is greater than the maximum availed power may include determining if the current drawn by the medical device and the subsystem devices is greater than the maximum current that can be drawn from the power supply (e.g., determined based on the rating of the power supply). In another form of the present technology, the determination of whether the power used is greater than the maximum availed power may include determining if the sum of current drawn by the medical device and the target current settings for the subsystem devices is greater than the maximum current that can be drawn from the power supply.

If the power used is greater than the maximum available power (YES in step 5404), then new power settings for one or more subsystem devices may be updated (step 5412) so that the total power used does not exceed the maximum power. If the power used is not greater than the maximum available power (NO in step 5404), then the present power settings may be maintained or adjusted to use the excess available power. If banking is not enabled (NO in step 5406), then the power settings are transmitted to the devices or device controllers (step 5410) without being updated. If banking is enabled (YES in step 5406), then power settings may be updated for one or more subsystem devices to use the excess power available from the power supply.

Banking may include using excess power to control the subsystem components such that their power consumption exceeds the previously determined power settings. Excess power may include power that is available before the over protection of the power supply is triggered. For heating elements, banking may include increasing the power so that additional heat is generated during period when excess power is available to compensate for heat not generated during periods when power was limited so that devices with higher priority could be powered. Banking may be enabled based on a user controls and/or type of power supply connected (e.g., when a power supply with low power is connected).

When power provided to the subsystem components is reduced because the total power used is greater than the maximum available power (YES in step 5405), a calculation may be made to determine how much power is not provided due to the power limitations and should be added when additional power is available. The amount of power "debited" for the subsystem components during the reduction in power may be provided by Expected Power minus Actual Power Provided. The expected power may represent the power that the system determines is needed to be provided to the subsystem components. The actual power provided may represent the power provided to the subsystem components after a reduction in the power supplied to the subsystem components. When extra power is available (NO in step 5404) and Banking is enabled (YES in step 5406), the debited power may be added to the power already being provided to the subsystem components.

In one example, a duration of time that power is not provided to the heating elements may be accumulated when the power is limited to the heating elements, and when extra power is available, the duty cycle of the power signals provided to the heating elements may be increased to provide additional power for the duration of accumulated time.

Banking may be enabled when there is a need to improve the stability of heating control or its accuracy compared to target performance Banking may provide an advantage in performance of heaters for which there is no feedback from a corresponding sensor. For example, if the subsystem for heating a plate to evaporate water has no downstream sensor indicating the amount of water evaporated, then when heating is suppressed as lower priority, the evaporation rate falls short of the target. With no feedback to the controller, there is no stimulus to raise the overall average heating. Banking provides this compensation to maintain the intended rate of evaporation.

Banking may provide an advantage when the feedback from a sensor is slow. For example, the subsystem for heating a tube receives feedback from a gas temperature sensor. When heating is suppressed as lower priority, the gas temperature may fall from target. Feedback from the sensor will stimulate the controller to increase heating when power is available, with some lag in the response. Banking can accelerate this response by anticipating the fall in gas temperature before the sensor indicates it. Thus banking provides less variation in gas temperature delivered to the patient.

Updating the power setting for one or more subsystem devices (step 5412) may include determining the current setting for the one or more subsystem devices. A PI controller may use this current setting to determine and update (based on measured current) the duty cycle for the respective subsystem device. In one form of the present technology, updating the power settings may include determining the duty cycle for the respective subsystem device. The current or duty cycle may be reduced if the power being used is greater than the maximum available power. The current or duty cycle may be increased if the extra power is available and banking is enabled.

FIGS. 5O and 5P show more detailed methods for executing adaptive power management according to various forms of the present technology. In one form of the present technology, the method may be executed by software and/or hardware. The methods may be executed by a processing system including one or more processors. In one form of the present technology, the methods may be executed at least partially by a central controller 4230. In some implementations of the present technology, the power management methods illustrated in FIGS. 5O and 5P may be entirely performed by software.

FIG. 5O shows adaptive power management performed based on measured currents and set currents for subsystem devices (e.g., heater plate 5020 and/or the heated tube 4172). An ADC driver may be configured to measure current channels of the medical device for computing the current $I_{FG\ M}$ representing the measured current drawn by the system excluding the one or more subsystem devices, current $I_{PLATE\ M}$ representing the current drawn by a first subsystem device (e.g., a heater plate 5020), and/or current $I_{TUBE\ M}$ representing the current drawn by a second subsystem device (e.g., a heated tube 4172).

The method may include obtaining the power supply maximum available current $I_{MAX}$. $I_{MAX}$ may be based on the rating of the power supply. In some exemplary implementations, $I_{MAX}$ may be based on the overprotection values of the power supply. Current $I_{MAX}$ may be stored in a memory, determined by software and/or hardware based on a type of power supply coupled to or included in the medical device, determined based on power stored in the power supply, and/or received from the power supply or another component in the medical device. $I_{MAX}$ may be dynamically changed depending which power supply (e.g., 65 W and 90 W) is connected to flow generator. $I_{MAX}$ for a given power supply may be a constant value (e.g., a pre-stored value for a given power supply). The type of power supply may be determined based on an indicator (e.g. a resistor and/or a chip) included in the power supply. For example, a different resistor value may indicate a different power supply or functionality of the power supply. A chip included in the power supply may provide a code indicating a different power supply or functionality of the power supply. As discussed above, the power supply may include AC/DC power pack, DC/DC converter, and/or portable battery pack. While $I_{MAX}$ may not take into account the overprotection values of the power supply, in some implementations, the timing for controlling currents of the heater plate and/or heated tube may be well below the OCP window before protection circuit is tripped.

In some implementations, for example in a battery pack, $I_{MAX}$ may derate due to being low on a charge, environmental changes (e.g., temperature, pressure), number of cycles, and/or peak currents. In some implementations, the power supply may be configured to dynamically determined $I_{MAX}$ and provide a signal to indicate $I_{MAX}$ value. In some implementation, the system may include a circuit and/or sensors to dynamically determine $I_{MAX}$. The available charge and/or environmental conditions may be measured to determine $I_{MAX}$.

The method may include obtaining the currents set for the one or more subsystem devices (e.g., heater plate 5020 and/or the heated tube 4172). In one example, the set currents include the heater plate current set point $I_{PLATE\ SP}$ and heated tube current set point $I_{TUBE\ SP}$. The set currents may be determined based on the duty cycle set point used to control the operation of the subsystem devices.

The duty cycle set points may be set according to a climate control algorithm. The climate control algorithms disclosed in U.S. Pat. No. 9,802,022 titled "Humidification of Respiratory Gases" and methods for controlling the duty cycle disclosed in U.S. Pat. No. 8,844,522 "Power Management in Respiratory Treatment Apparatus", both of which are incorporated herein by reference, may be used to set and control the duty cycle set point for the subsystem devices (e.g., heater plate 5020 and/or the heated tube 4172). In some implementations of the present technology, humidifier and heated tube control algorithms disclosed in FIGS. 15-18 of U.S. Pat. No. 9,802,022 titled "Humidification of Respiratory Gases" may be used to control the operation of the heater plate and/or heated tube.

In one example, the duty cycle set point determined by a climate control algorithm for the heater plate 5020 may be converted to obtain the heater plate current set point $I_{PLATE\ SP}$, and the duty cycle set point determined by a climate control algorithm for the heated tube 4172 may be converted to obtain the heated tube current set point $I_{TUBE\ SP}$.

The method illustrated in FIG. 5O, may include determining whether the current being used exceeds the power supply maximum available current $I_{MAX}$. The current being used may be represented by a sum of current $I_{FG\_M}$ representing the measured current drawn by the system excluding the one or more subsystem devices, the heater plate current set point $I_{PLATE\ SP}$, and the heated tube current set point $I_{TUBE\ SP}$. The advantages of using the current set point instead of the measured currents for the heater plate and the heated tube is that more accurate results may be provided. Using the measured currents may provide incorrect results, as the measured currents reduce in proportion to the duty cycle set by the controller, so they do not correspond to the targets of the controller.

If the current being used exceeds the power supply maximum available current $I_{MAX}$, then new heater plate and heated tube current set point currents can be computed by reducing the power that will be used by the heater plate and the heated tube. In some example, priority may be given to the heated tube over the heater plate (e.g., with a 60 to 40% ratio). If the current being used does not exceed the power supply maximum available current $I_{MAX}$ and current banking is enabled, then extra current may be used to adjust the settings from the one or more subsystem devices. The extra current may be computed by subtracting the sum of current $I_{FG\ M}$, the heater plate current set point $I_{PLATE\ SP}$, and heated tube current set point $I_{TUBE}$ from power supply maximum available current $I_{MAX}$. With extra current available, new heater plate and heated tube current set point currents can be computed to use the extra available current. In some example, priority may be given to the heated tube over the heater plate (e.g., with a 60 to 40% ratio).

The new heater plate current set point $I_{PLATE\ SP}$ and the heated tube current set point $I_{TUBE\ SP}$, may be used to control the heater plate and the heated tube controllers. In one example, the heater plate and the heated tube controllers may comprise PI controllers set based on the measured currents (e.g., $I_{PLATE\ M}$ and $I_{TUBE\ M}$) and the set currents (e.g., $I_{PLATE\ SP}$ and $I_{TUBE\ SP}$). The PI controller for the heated tube may set the heated tube duty cycle based on $I_{TUBE\ SP}$ and $I_{TUBE\ M}$. The PI controller for the heater plate may set the heater plate duty cycle based on $I_{PLATE\ SP}$ and $I_{PLATE\ M}$. The determined duty cycles may be applied to the respective subsystem devices in real time (e.g., every cycle).

If the current being used does not exceed the power supply maximum available current $I_{MAX}$ and current banking is not enabled, then the existing current settings can be maintained. In this case, the existing heater plate current set point $I_{PLATE\ SP}$ and the heated tube current set point $I_{TUBE\ SP}$ may be used to control the heater plate and the heated tube controllers.

The rate of the climate control cycle may be at a relatively slow rate (e.g. every 1 s) as is appropriate to manage the slow thermal response of heated subsystems. The rate of the active power management cycle (e.g. each 500 μs) is preferably faster than the most rapid increase in current consumption by a high priority load. For example, FG current $I_{FGM}$ may rise rapidly to accelerate the blower to increase airflow when a patient inhales.

In the above examples, the heated tube and plate heater current closed loops are used instead of a duty cycle. While it may be easy to estimate the current drawn by the tube (or plate) according to the duty cycle applied, the disadvantage is that this calculation can be very inaccurate because the estimated current is highly dependent of the resistance tolerance and temperature of the part. For example, the test results relying on duty cycle show that the system can deliver less power to the plate and the tube than expected. This inaccuracy may lead the active power management to clip the humidifier or heated tube power too early. Using a faster current closed loop for the heater plate and/or the heated tube may improve the overall performance of the humidification.

In one form of the present technology, the duty cycle range for PWM of the heated tube and/or the heater plate may have a duty cycle range from 0 to 99%. In some examples, 100% duty cycle may not be allowed by the hardware.

As discussed above, the heated tube and/or the heated plate may use a PI controller. The PI controllers may use the difference between the current set point and the current measured to compute a duty cycle output for the heated tube and/or the heated plate.

Because the output offset of an operational amplifiers used for current measurement may be quite high (~160 mV), they may not allow the measurement of current lower than 200 mA. Accordingly, the PI controller may not be used at low duty cycles. When the current set point is lower than a pre-set value (e.g., 10% of the maximum current), a fixed duty cycle may be applied (e.g. 10%) and a fake current measurement may be computed (e.g. 10% of the maximum current). The current set point may be 283 mA (=10% of 2.83 A) for the plate and 240 mA (=10% of 2.40 A) for the tube, in some examples.

FIG. 5P shows adaptive power management performed based on measured currents and set power for subsystem devices (e.g., heater plate 5020 and/or the heated tube 4172). As discussed below with reference to FIG. 5P, some implementations of the present technology may include a power control closed loop the settings of which may be used to calculate the set point currents of the subsystem devices. The discussion of operations illustrated in FIG. 5O which are similar to operations illustrated in FIG. 5P, may be applied to the adaptive power management operations illustrated in FIG. 5P.

RPT device 4000 may include a power control closed loop, which may be embedded in a microcontroller. The power control closed loop may use the flow generator duty cycle outputs as percentage of power set point. Each percentage may have a range of 0 to 100% out of the available power (e.g., 60 W power range). The duty cycle applied to the plate (or tube) may be calculated by: Duty Cycle=power set point/(supplied voltage measured*$I_{PEAK}$ measured). This formula may not be applicable if the duty cycle is low because the current may not reach its peak due to the high plate (or tube) inductance. In this situation, Ipeak may not be measured but calculated using the resistance of the plate (or tube): I=supplied voltage measured/Resistance. The resistance may be calculated using the temperature of the plate (or tube).

As illustrated in FIG. 5P, in some implementations of the present technology, the power set points may be output by the Climate Control algorithm at predetermined intervals (e.g., every second). The power set points are used to control the operation of the plate and tube powers. The power set points and the measured power of the pressure system are used to determine the current set points. In the adaptive power management, the tube and plate current set points may be computed by: Current set point=Power set point/supply voltage measured. The supply voltage may be measured by the pressure system software every 10 ms and used by the adaptive power management every 0.5 ms. In this implementation, the system can accurately take into account changes to the voltage source due to the operation of the blower.

Both tube and plate duty cycles may be output by the existing PI current close loop controllers.

Unlike other approaches for controlling the medical device and the subsystem devices, some implementations of adaptive power management according to the present technology do not predict when the patient will inhale, but use real time power use measurements and power settings to determine how the devices are controlled. The present technologies provide for fast detection of how power is being used by the various subsystems of the medical device. For example, when inhalation begins, operation of the blower is changed and detected by a sensing circuit. This change in operation may trigger to reduce heater power so that additional power is available for the blower. The blower does not have to wait for the heater to reduce the power before it spins up, as the delay may be felt by the patient. The power management provides for fast response because if the heater power is held up for too long, the combined current draw can exceed the capacity of the power supply and trigger the current overprotection.

5.8 Breathing Waveforms

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min A typical duty cycle, the ratio of Ti to Ttot, is about 40%.

FIG. 6B shows selected polysomnography channels (pulse oximetry, flow rate, thoracic movement, and abdominal movement) of a patient during non-REM sleep breathing normally over a period of about ninety seconds, with about 34 breaths, being treated with automatic PAP therapy, and the mask pressure being about 11 cmH$_2$O. The top channel shows pulse oximetry (oxygen saturation or SpO$_2$), the scale having a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electo-cardiogram. The seventh channel shows pulse oximetry (SpO$_2$) with repetitive desaturations to below 70% from about 90%. The eighth channel is respiratory airflow using a nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

FIG. 6D shows patient flow rate data where the patient is experiencing a series of total obstructive apneas. The duration of the recording is approximately 160 seconds. Flow rates range from about +1 L/s to about −1.5 L/s. Each apnea lasts approximately 10-15 s.

FIG. 6E shows a scaled inspiratory portion of a breath where the patient is experiencing low frequency inspiratory snore.

FIG. 6F shows a scaled inspiratory portion of a breath where the patient is experiencing an example of flattened inspiratory flow limitation.

FIG. 6G shows a scaled inspiratory portion of a breath where the patient is experiencing an example of "mesa" flattened inspiratory flow limitation.

FIG. 6H shows a scaled inspiratory portion of a breath where the patient is experiencing an example of "panda ears" inspiratory flow limitation.

FIG. 6I shows a scaled inspiratory portion of a breath where the patient is experiencing an example of "chair" inspiratory flow limitation.

FIG. 6J shows a scaled inspiratory portion of a breath where the patient is experiencing an example of "reverse chair" inspiratory flow limitation.

FIG. 6K shows a scaled inspiratory portion of a breath where the patient is experiencing an example of "M-shaped" inspiratory flow limitation.

FIG. 6L shows a scaled inspiratory portion of a breath where the patient is experiencing an example of severely "M-shaped" inspiratory flow limitation.

FIG. 6M shows patient data from a patient with Cheyne-Stokes respiration. There are three channels: pulse oximetry (SpO$_2$); a signal indicative of flow rate; and thoracic movement. The data span six minutes. The signal representative of flow rate was measured using a pressure sensor connected to a nasal cannula. The patient exhibits apneas of about 22 seconds and hyperpneas of about 38 seconds. The higher frequency low amplitude oscillation during apnea is cardiogenic.

FIG. 6N shows patient data from a patient with another example of Cheyne-Stokes respiration, using the same three channels as in FIG. 6M. The data span ten minutes. The patient exhibits hyperpneas of about 30 seconds and hypopneas of about 30 seconds.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.9.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.10 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| | |
|---|---|
| patient | 1000 |
| bed partner | 1100 |
| edition published | 2012 |
| compact power supply | 2410 |
| patient interface | 3000 |
| seal - forming structure | 3100 |
| plenum chamber | 3200 |
| structure | 3300 |
| vent | 3400 |
| connection port | 3600 |
| forehead support | 3700 |
| ISO | 3744 |
| RPT device | 4000 |
| external housing | 4010 |
| upper portion | 4012 |
| portion | 4014 |
| panel s | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| heated air circuit | 4171 |
| tube | 4172 |
| supplemental oxygen | 4180 |
| electrical components | 4200 |
| PCBA | 4202 |
| power supply | 4210 |
| input device | 4220 |
| central controller | 4230 |
| clock | 4232 |
| therapy device controller | 4240 |
| protection circuit | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| pre - processing module | 4310 |
| pressure compensation | 4312 |
| vent flow rate estimation | 4314 |
| leak flow rate estimation | 4316 |
| respiratory flow rate estimation | 4318 |
| therapy engine module | 4320 |
| phase determination | 4321 |
| waveform determination | 4322 |
| ventilation determination | 4323 |
| inspiratory flow limitation determination | 4324 |
| apnea/hypopnea determination | 4325 |
| snore determination | 4326 |
| airway patency determination | 4327 |
| target ventilation determination | 4328 |
| therapy parameter determination | 4329 |
| therapy control module | 4330 |
| methods | 4340 |
| humidifier | 5000 |
| humidifier inlet | 5002 |

-continued

| | |
|---|---|
| humidifier outlet | 5004 |
| humidifier base | 5006 |
| heater | 5020 |
| reservoir | 5110 |
| conductive portion | 5120 |
| humidifier reservoir dock | 5130 |
| locking lever | 5135 |
| water level indicator | 5150 |
| humidifier transducers | 5210 |
| air pressure sensor | 5212 |
| air flow rate transducer | 5214 |
| temperature transducers | 5216 |
| humidity sensor | 5218 |
| heating element | 5240 |
| humidifier controller | 5250 |
| central humidifier controller | 5251 |
| heating element controller | 5252 |
| air circuit controller | 5254 |
| current sensing circuit | 5302 |
| current sensing circuit | 5304 |
| current sensing circuit | 5306 |
| current sensing circuit | 5308 |
| blower controller | 5310 |
| heater plate controller | 5312 |
| tube controller | 5314 |
| power use data step | 5402 |
| step | 5404 |
| step | 5405 |
| step | 5406 |
| step | 5410 |
| step | 5412 |
| step | 5502 |
| step | 5504 |
| step | 5506 |
| step | 5508 |
| step | 5510 |
| step | 5512 |
| waveform | 6010 |
| waveform | 6020 |
| waveform | 6030 |
| waveform | 6040 |
| op - amp | 6050 |
| op - amp | 6052 |
| op - amp | 6054 |
| capacitor | 6066 |
| resistor | 6068 |
| voltage controlled PWM circuit | 6070 |
| gate | 6072 |
| gate | 6074 |

The invention claimed is:

1. A respiratory treatment apparatus comprising:
a power supply;
a pressure generator configured to generate a flow of air;
a heating element configured to heat the generated flow of air;
one or more sensors configured to generate sensor signals representing a property of the flow of air; and
a processing system comprising one or more processors and configured to:
receive the sensor signals;
based on the received sensor signals, determine a control signal for controlling the heating element;
receive signals corresponding to current drawn by the pressure generator;
receive signals corresponding to current drawn by the heating element;
based on the current drawn by the pressure generator and the current drawn by the heating element not exceeding a maximum current of the power supply, modify the control signal for controlling the heating element to cause the heating element to draw more current than the current that would be drawn with the determined control signal; and control operation of the heating element using the modified control signal for controlling the heating element.

2. The respiratory treatment apparatus of claim 1, wherein a power that could be drawn by the pressure generator and the heating element combined exceeds the capability of the power supply.

3. The respiratory treatment apparatus of claim 1, wherein when a sum of current drawn by the pressure generator and current that would be drawn by the heating element using the determined control signal for the heating element exceeds the maximum current of the power supply, the control signal for controlling the beating element is modified such that the modified control signal will cause the heating element to draw less current than the current that would be drawn with the determined control signal.

4. The respiratory treatment apparatus of claim 1, wherein at least one of the one or more sensors is configured to generate sensor signals representing temperature of the air flow and the processing system is further configured to control the pressure generator based on the sensor signals representing temperature of the flow of air, and the flow of air is delivered to a patient interface via a tube coupled to the flow generator.

5. The respiratory treatment apparatus of claim 1, wherein at least one of the one or more sensors is a pressure sensor configured to generate sensor signals representing pressure of the air flow and the control signal for controlling the heating element is determined based on the sensor signals representing pressure of the flow of air.

6. The respiratory treatment apparatus of claim 1, wherein at least one of the one or more sensors is a flow sensor configured to generate sensor signals representing flow of the air flow and the processing system is configured to control the pressure generator based on the sensor signals representing flow of the flow of air and the control signal for controlling the heating element is determined based on the sensor signals representing flow of the flow of air.

7. The respiratory treatment apparatus of claim 1, wherein the modified control signal for controlling the heating element is controlled to accrue a heat deficit in a time period and return the accrued heat deficit in a subsequent time period.

8. The respiratory treatment apparatus of claim 1, wherein the modified control signal for controlling the heating element decreases the heat produced by the heating element during a first period and increases the heat produced by the heating element during a second period following the first period.

9. The respiratory treatment apparatus of claim 8, wherein during the first period the power of the power supply equals the power consumed by the pressure generator and the heating element and/or during the second period the power of the power supply exceeds the power consumed by the pressure generator and the heating elemental.

10. An apparatus for treating a respiratory disorder in a patient, the apparatus comprising:
a power supply;
a pressure generator configured to generate a flow of breathable gas;
a humidifier comprising a first heating element and configured to humidify the breathable gas;
a second heating element configured to heat the humidified breathable gas in a hose configured to deliver the humidified breathable gas to the patient;
a sensor configured to generate a flow signal representing a property of the flow of breathable gas;
a controller configured to:
based on the flow signal, determine a first control signal for controlling the first heating element, and a second control signal for controlling the second heating element;
based on (1) measured current drawn by the pressure generator during operation of the pressure generator, (2) the first control signal, and (3) the second control signal, determine if power to be used by the apparatus;
if it is determined that the power to be used by the apparatus exceeds a peak power of the power supply, modify the first control signal and/or the second control signal to decrease the power used by the first heating element and/or the second heating element; and
if it is determined that the power to be used by the apparatus does not exceed the peak power of the power supply, modify the first control signal and/or the second control signal to increase the power used by the first heating element and/or the second heating element.

11. The apparatus of claim 10, wherein the first and second control signals are pulse width modulated signals.

12. The apparatus of claim 10, wherein the first control signal is a first pulse width modulated signal and the second control signal is a second pulse width modulated signal that is offset in time from the first pulse width modulated signal.

13. The apparatus of claim 10, wherein, if it is determined that the power to be used by the apparatus does not exceed the peak power of the power supply, the first control signal and the second control signal are modified to increase the power used by the first heating element and the second heating element with priority given to the second heating element.

14. The apparatus of claim 10, wherein, if it is determined that the power to be used by the apparatus exceeds the peak power of the power supply, modify the first control signal and the second control signal to decrease the power used by the first heating element and the second heating element with priority given to the second heating element.

15. The apparatus of claim 10, wherein the first control signal is a first current set point provided to a proportional, proportional-differential, or proportional-integral controller configured to control operation of the first heating element, and the second control signal is a second current set point provided to a proportional, proportional-differential, or proportional-integral controller configured to control operation of the second heating element.

16. The apparatus of claim 10, wherein determining if power to be used by the apparatus exceeds a peak power of the power supply includes determining whether a sum of (1) a current drawn by the apparatus without the current drawn by the first and second heating elements, (2) a current that would be drawn by the first heating element using the determined first control signal, and (3) a current that would be drawn by the second heating element using the determined second control signal, is greater than a maximum current that can be provided by the power supply.

17. The apparatus of claim 10, wherein the flow signal corresponds to a patient's respiratory cycle during use of the apparatus and the first control signal and the second control signal are determined to control offsetting peak power operation of the first heating element and the second heating element based on the flow signal.

18. The apparatus of claim 10, wherein the power of the power supply is lower than the power that would be simultaneously drawn by the pressure generator, the first heating element using the first control signal, and the second heating element using the second control signal.

19. A method of operating a respiratory treatment apparatus comprising a pressure generator for generating a flow of breathable gas in order to treat a respiratory disorder, the method comprising:
   receiving, from one or more sensors configured to generate sensor signals representing a property of the flow of breathable gas, the sensor signals;
   based on the received sensor signals, determining a control signal for controlling a heating element configured to heat the generated flow of breathable gas;
   receiving signals corresponding to current drawn by the pressure generator;
   receiving signals corresponding to current drawn by the heating element;
   based on the current drawn by the pressure generator and the current drawn by the heating element not exceeding a maximum current of a power supply of the respiratory treatment apparatus, modifying the control signal for controlling the heating element to cause the heating element to draw more current than the current that would be drawn with the determined control signal; and
   controlling operation of the heating element using the modified control signal for controlling the heating element.

20. The method of claim 19, wherein a power that can be drawn by the pressure generator and the heating element combined exceeds the capability of the power supply.

21. The method of claim 19, wherein when a sum of current drawn by the pressure generator and current that would be drawn by the heating element using the determined control signal for the heating element exceeds the maximum current of the power supply, the control signal for controlling the heating element is modified such that the modified control signal will cause the heating element to draw less current than the current that would be drawn with the determined control signal.

* * * * *